(12) United States Patent
Milanova

(10) Patent No.: US 12,357,510 B2
(45) Date of Patent: Jul. 15, 2025

(54) TUBULAR TAMPON AND METHOD OF MANUFACTURING SAME

(71) Applicant: Anne's Day Ltd, London (GB)

(72) Inventor: Valentina Milanova, London (GB)

(73) Assignee: Anne's Day Ltd, London (GB)

( * ) Notice: Subject to any disclaimer, the term of this patent is extended or adjusted under 35 U.S.C. 154(b) by 478 days.

(21) Appl. No.: 17/571,423

(22) Filed: Jan. 7, 2022

(65) Prior Publication Data

US 2022/0218535 A1 Jul. 14, 2022

Related U.S. Application Data

(60) Provisional application No. 63/135,247, filed on Jan. 8, 2021.

(51) Int. Cl.
*A61F 13/20* (2006.01)
*A61F 13/34* (2006.01)

(52) U.S. Cl.
CPC ...... *A61F 13/2042* (2013.01); *A61F 13/2051* (2013.01); *A61F 13/2071* (2013.01); *A61F 13/2088* (2013.01); *A61F 13/2094* (2013.01); *A61F 13/34* (2013.01)

(58) Field of Classification Search
CPC .............. A61F 13/2085; A61F 13/2088; A61F 13/2094; A61F 13/2042; A61F 13/2071; A61F 13/34; A61F 13/206; A61F 13/2091; A61F 13/2051; A61F 13/2028
USPC ............................................ 28/118, 119, 120
See application file for complete search history.

(56) References Cited

U.S. PATENT DOCUMENTS

| | | | | | |
|---|---|---|---|---|---|
| 2,330,257 | A | * | 9/1943 | Bailey | A61F 13/2037 604/377 |
| 2,440,141 | A | * | 4/1948 | Donovan | A61F 13/2051 15/210.1 |
| 3,815,601 | A | * | 6/1974 | Schaefer | A61F 13/2051 604/385.18 |
| 3,818,912 | A | * | 6/1974 | Etz | A61F 13/2085 604/904 |
| 3,875,615 | A | * | 4/1975 | Muckenfuhs | A61F 13/2085 28/119 |
| 4,018,225 | A | * | 4/1977 | Elmi | A61F 13/2037 604/377 |

(Continued)

*Primary Examiner* — Amy Vanatta
(74) *Attorney, Agent, or Firm* — Cognition IP, P.C.; Edward Steakley; Justin White

(57) ABSTRACT

A tubular shaped tampon can include an absorbent body defining a cylindrical shape having a hollow interior, a porous protective sleeve surrounding the absorbent body, and a string that holds the protective sleeve in place against the absorbent body and facilitates removal of the tampon after use. The absorbent body and protective sleeve can combine to define an overall tubular structure having an inner hollow region, providing increased surface area. Methods of manufacturing the tampon can include cutting a fluid absorbent material, rolling the cut material around elongated machine prongs to form an absorbent body, rolling a porous sheet around and extending beyond both distal ends of the absorbent body, pinching together distal ends of the porous sheet, pushing at least one distal end through the hollow interior of the absorbent body, stitching the distal ends of the porous sheet together, and punching a string through the protective sleeve and absorbent body.

12 Claims, 22 Drawing Sheets

(56) References Cited

U.S. PATENT DOCUMENTS

| | | | | |
|---|---|---|---|---|
| 4,222,381 | A | * | 9/1980 | Widlund ............... A61F 13/206 |
| | | | | 604/379 |
| 4,475,911 | A | * | 10/1984 | Gellert ................ A61F 13/2037 |
| | | | | 604/371 |
| 4,816,100 | A | * | 3/1989 | Friese .................. A61F 13/206 |
| | | | | 156/194 |
| 5,201,326 | A | * | 4/1993 | Kubicki ................ A61L 15/32 |
| | | | | 424/431 |
| 7,387,622 | B1 | * | 6/2008 | Pauley ................ A61F 13/2082 |
| | | | | 604/385.18 |
| 2002/0026177 | A1 | * | 2/2002 | Lochte .................... A61F 13/26 |
| | | | | 28/118 |
| 2002/0107497 | A1 | * | 8/2002 | Osborn, III ......... A61F 13/2051 |
| | | | | 604/385.18 |
| 2008/0221502 | A1 | * | 9/2008 | Binner ................ A61F 13/2085 |
| | | | | 604/385.18 |
| 2013/0067707 | A1 | * | 3/2013 | Kaiser ................ A61F 13/2082 |
| | | | | 28/118 |
| 2014/0115845 | A1 | * | 5/2014 | Tomsovic ........... A61F 13/2071 |
| | | | | 28/118 |

* cited by examiner

TUBULAR TAMPON AND METHOD OF MANUFACTURING SAME

CROSS-REFERENCE TO RELATED APPLICATIONS

This application claims the benefit of U.S. Provisional Application No. 63/135,247, filed Jan. 8, 2021, which are hereby incorporated by reference in their entirety.

TECHNICAL FIELD

The present disclosure relates generally to feminine hygiene products, and more particularly to tampons and methods of manufacturing tampons.

BACKGROUND

Tampons and other feminine hygiene products have worked for many years to absorb and block menstrual fluids conveniently. After absorbing sufficient amounts of fluid, most tampons begin to expand, eventually resulting in the need to remove and/or replace the tampon with another tampon or product. Tampons are typically made by folding or rolling rectangular strips of absorbent material into a blank and then compressing the blank into a cylindrical shape. A withdrawal string can be attached for removal, and an applicator may or may not be used as well. The tampon can then be wrapped and packaged for sale, which may include assembly into an applicator.

Due to their typical structural nature, all of the absorbent material in most tampons does not become fully saturated and the tampons do not expand uniformly during typical use. Reduced absorption and uneven expansion can result in inefficiencies, discomfort, and leakage. Furthermore, the absorbent material in most tampons can be partially or even fully unshielded, which can result in the messy and sometimes unsafe shedding of fibers in some cases.

Although traditional ways of designing and manufacturing tampons have worked well in the past, improvements are always helpful. In particular, what is desired are improved tampons that are safer and more comfortable to use through reduced fiber loss, enhanced absorption, and more uniform expansion, as well as ways for manufacturing such tampons.

SUMMARY

It is an advantage of the present disclosure to provide improved tampons that are safer and more comfortable to use, among other benefits. The disclosed features, apparatuses, systems, and methods provide improved tampon products and tampon manufacturing solutions that involve tampon products having reduced fiber loss, enhanced absorption, and more uniform expansion. These advantages can be accomplished at least in part by forming tubular shaped tampons that include an outer surface area as well as an inner surface area, and by using multiple sets of machine prongs in the manufacturing process to readily form such tampon products.

In various embodiments of the present disclosure, a tampon can include an absorbent body, a protective sleeve, and a string. The absorbent body can be formed of a fluid absorbent material and can define a cylindrical shape having an exterior surface, a hollow interior, an interior surface, and first and second opposing distal ends. The protective sleeve can surround the absorbent body at both the exterior surface and interior surface and can be porous to allow fluid to enter the absorbent body but prevent absorbent body material from passing through the protective sleeve. The absorbent body and protective sleeve can combine to define an overall tubular structure having an inner hollow region. The string can be coupled to the protective sleeve and absorbent body to facilitate removal of the tampon after use. Added stitching and/or the string can hold the protective sleeve in place against the absorbent body.

In various detailed embodiments, the protective sleeve can wrap continuously around both distal ends of the absorbent body. This can involve stitching to fasten extended ends of the protective sleeve together once the sleeve has wrapped around the absorbent body. Alternatively, this can involve a first end of the protective sleeve being tucked beneath another portion of the protective sleeve at the interior surface of the absorbent body at the first distal end of the absorbent body and a second end of the protective sleeve extending past the interior surface of the absorbent body at the second distal end of the absorbent body. The string can extend from a top outer surface of the protective sleeve through the protective sleeve, a top portion of the absorbent body, an inner surface of the protective sleeve, the hollow region, another inner surface of the protective sleeve, a bottom portion of the absorbent body, and out from a bottom outer surface of the protective sleeve. In various arrangements, the absorbent material can be cotton, which can be compressed. The protective sleeve can be a thin sheet of nonwoven cotton fiber fabric.

In further embodiments of the present disclosure, various methods of creating a tampon are provided. Pertinent method steps can include forming an absorbent body defining a cylindrical shape having an exterior surface, a hollow interior, an interior surface, and first and second opposing distal ends, the absorbent body having a fluid absorbent material, enclosing the absorbent body within a protective sleeve at the exterior surface, interior surface, and both distal ends, the protective sleeve being porous to allow fluid to enter the absorbent body but prevent absorbent body material from passing through the protective sleeve, wherein the absorbent body and protective sleeve combine to define an overall tubular structure having an inner hollow region and a first diameter, and coupling a string to the protective sleeve.

In various detailed embodiments, additional steps can include compressing the overall tubular structure to a second diameter that is less than the first diameter and/or applying a coating to an outer surface of the overall tubular structure. Forming the absorbent body can include cutting a fluid absorbent material, which can be cotton, to a specific length and width, rolling the cut fluid absorbent material around a first set of elongated machine prongs, and removing the first set of elongated machine prongs.

Enclosing the absorbent body within the protective sleeve can include rolling a porous sheet around the absorbent body, wherein the porous sheet extends beyond both distal ends of the absorbent body at a length that exceeds the length of the absorbent body, pinching together a first distal end of the porous sheet that extends beyond the first distal end of the absorbent body, pushing the pinched together first distal end of the porous sheet through the hollow interior and past the second distal end of the absorbent body, stitching together the protective sleeve ends that extend past the absorbent body, and trimming away any excess protective sleeve material past the stitch.

In alternative arrangements, a stitch can be foregone in favor of pinching together a second distal end of the porous sheet that extends beyond the second distal end of the absorbent body, and pushing the pinched together second distal end of the porous sheet through the hollow interior and past the first distal end of the absorbent body, wherein pushing the second distal end of the porous sheet tucks the first distal end of the porous sheet between the porous sheet and the absorbent body. Pinching together the first distal end of the porous sheet and pushing the pinched together first distal end can be performed by a second set of elongated machine prongs. The steps of removing the first set of elongated machine prongs and pushing the pinched together first distal end by a second set of elongated machine prongs can be performed simultaneously. Pinching together the second distal end of the porous sheet and pushing the pinched together second distal end can be performed by the first set of elongated machine prongs.

Coupling the string to the protective sleeve can include needle punching an end of the string through a top outer surface of the protective sleeve, pushing the string through the protective sleeve, a top portion of the absorbent body, an inner surface of the protective sleeve, the hollow region, another inner surface of the protective sleeve, a bottom portion of the absorbent body, and out from a bottom outer surface of the protective sleeve, and coupling the end of the string to a remaining portion of the string that has not passed through the protective sleeve. Coupling the end of the string can include passing the end of the string through a loop in the remaining portion of the string.

Other apparatuses, methods, features, and advantages of the disclosure will be or will become apparent to one with skill in the art upon examination of the following figures and detailed description. It is intended that all such additional apparatuses, methods, features and advantages be included within this description, be within the scope of the disclosure, and be protected by the accompanying claims.

BRIEF DESCRIPTION OF THE DRAWINGS

The included drawings are for illustrative purposes and serve only to provide examples of possible structures and arrangements for the disclosed apparatuses, systems and methods for tubular shaped tampons and methods of manufacturing same. These drawings in no way limit any changes in form and detail that may be made to the disclosure by one skilled in the art without departing from the spirit and scope of the disclosure.

DETAILED DESCRIPTION

Figure 1:
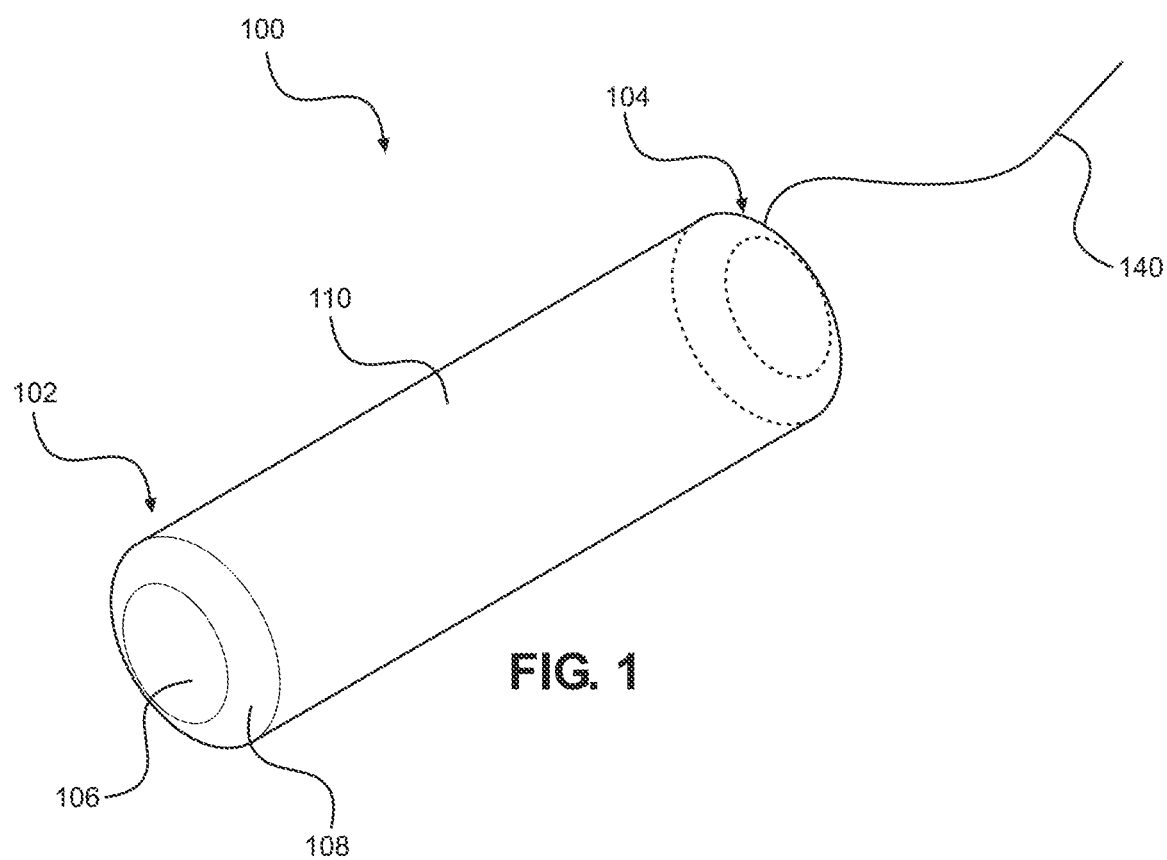
FIG. 1 illustrates in side perspective view an example finished tubular shaped tampon according to one embodiment of the present disclosure.

Exemplary applications of apparatuses, systems, and methods according to the present disclosure are described in this section. These examples are being provided solely to add context and aid in the understanding of the disclosure. It will thus be apparent to one skilled in the art that the present disclosure may be practiced without some or all of these specific details provided herein. In some instances, well known process steps have not been described in detail in order to avoid unnecessarily obscuring the present disclosure. Other applications are possible, such that the following examples should not be taken as limiting. In the following detailed description, references are made to the accompanying drawings, which form a part of the description and in which are shown, by way of illustration, specific embodiments of the present disclosure. Although these embodiments are described in sufficient detail to enable one skilled in the art to practice the disclosure, it is understood that these examples are not limiting, such that other embodiments may be used, and changes may be made without departing from the spirit and scope of the disclosure.

The present disclosure relates in various embodiments to features, apparatuses, systems, and methods for tubular shaped tampons and manufacturing such tubular shaped tampons. The disclosed embodiments can include the tampon products, as well as the methods of creating the tampon products. In particular, the disclosed embodiments can utilize different sets of machine prongs to form an absorbent material into a cylindrical or tubular shape, fully enclose the cylindrically shaped absorbent body within a protective sleeve, and couple a string to the protective sleeve and absorbent body such that the string can serve as an extraction device to facilitate removal of the tampon after use. Added stitching and/or the string can serve to hold the protective sleeve in place against the absorbent body.

Although various embodiments disclosed herein discuss tampons for use with an applicator, it will be readily appreciated that the disclosed features, apparatuses, systems, and methods can similarly be used for any relevant tampon or other feminine hygiene product with or without an applicator. For example, the disclosed methods can be used to form a tubular shaped tampon that may be inserted without an accompanying applicator. Furthermore, although different sets of machine prongs are described for the methods of manufacturing the disclosed tubular shaped tampons, it will be appreciated that any other elongated component or components can be similarly used to form the disclosed tampon products. Other applications, arrangements, and extrapolations beyond the illustrated embodiments are also contemplated.

It is an advantage of the present disclosure to provide improved tampons that are safer and more comfortable to use, among other benefits. The disclosed features, apparatuses, systems, and methods provide improved tampon products and tampon manufacturing solutions that involve tampon products having reduced fiber loss, enhanced absorption, and more uniform expansion. The disclosed tampons provide unique tubular structures that result in safer and more comfortable usage. Increased safety results from fully enclosing absorbent material within a protective sleeve such that little to no fiber loss can possibly occur during use.

While existing tampon products have fibrous absorbent material that is either fully exposed or at least exposed at a distal end or tip, the disclosed tampons fully wrap an absorbent material core within a protective sleeve. Increased comfort results from the enhanced absorbency, more uniform expansion, and reduced leakage that occur during use. While existing tampons absorb fluids inefficiently and expand unevenly, the disclosed tampons absorb fluids efficiently and expand evenly, resulting in greater comfort and less leakage. This is due to the tubular and cupped shape of the tampon, which is formed by pinching shut a back end of the tubular shaped tampon and holding it shut by stitching and/or a string attachment. With this shape, the front end of the tampon opens up like a cup as it starts to absorb fluid, which allows fluid to be more uniformly absorbed along the outer and inner surfaces of the tampon.

Starting with FIG. 1, an example finished tubular shaped tampon is illustrated in side perspective view. Tampon 100 can include a distal front end 102, distal back end 104, and inner hollow region 106. One or both distal ends 102, 104 can include a tapered region 108. Tampon 100 can include an overall tubular structure 110 and a string 140, which may be coupled at or proximate to distal back end 104. As set forth in greater detail below, overall tubular structure 110 can be formed from an absorbent body and a protective sleeve. The absorbent body can be formed of a fluid absorbent material defining a cylindrical shape having an exterior surface, a hollow interior, an interior surface, and first and second opposing distal ends. The protective sleeve can surround the absorbent body at both the exterior surface and interior surface, as well as at both distal ends. The protective sleeve can be porous to allow fluid to enter the absorbent body but prevent absorbent body material from passing through the protective sleeve. The string 140 can be coupled to the protective sleeve, the absorbent body, or both, and can facilitate removal of the tampon after use.

Figure 2:
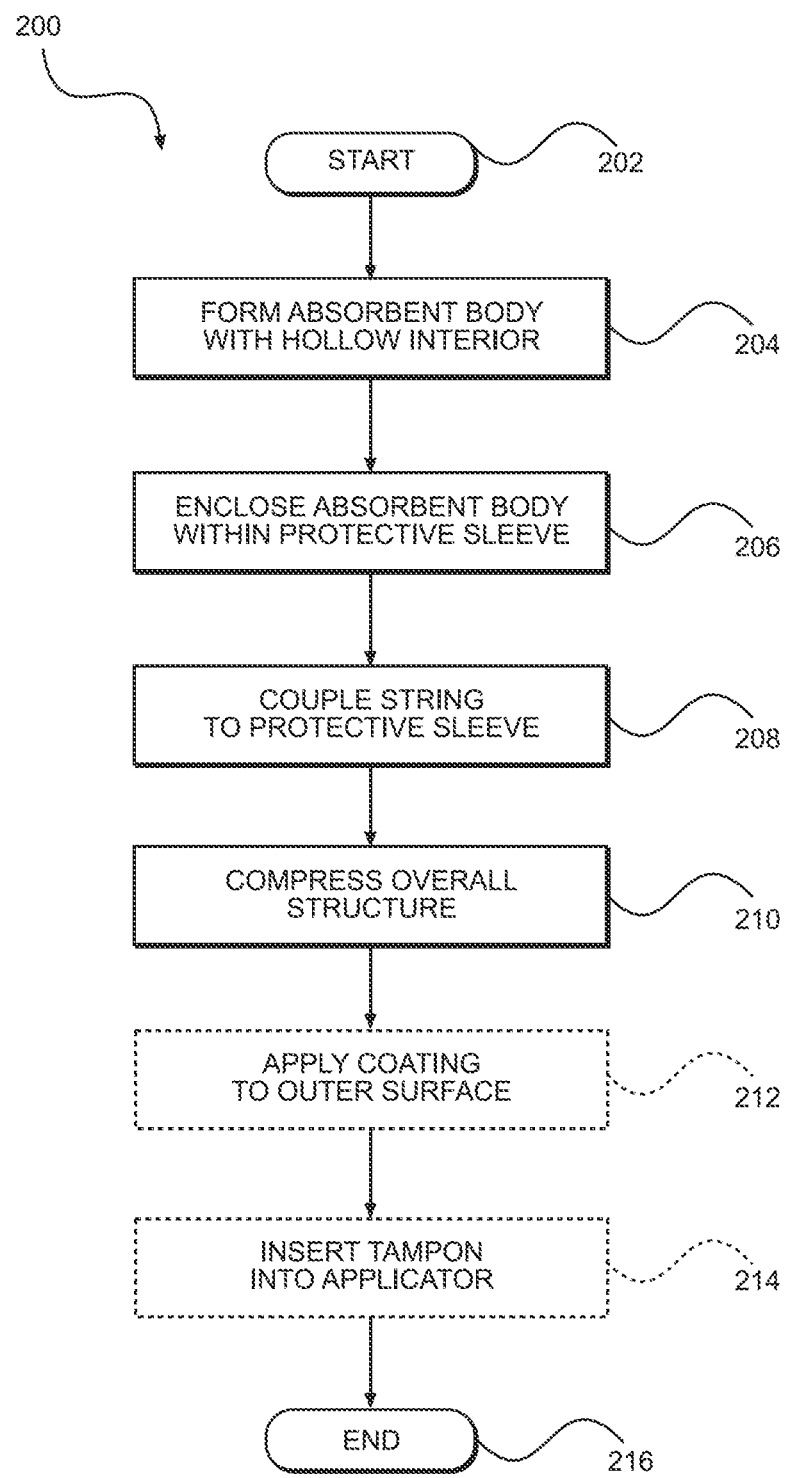
FIG. 2 illustrates a flowchart of an example method of creating a tampon according to one embodiment of the present disclosure.

Moving next to FIG. 2, a flowchart of an example method 200 of creating a tampon is provided. It will be appreciated that method 200 is a relatively high level process, and that various details are not provided at this point. After a start step 202, an absorbent body with a hollow interior is formed at process step 204. This can involve forming an absorbent body defining a cylindrical shape having an exterior surface, a hollow interior, an interior surface, and first and second opposing distal ends. The absorbent body can have a fluid absorbent material, such as, for example, natural organic cotton. Hemp and/or other suitable natural fiber materials may be mixed with the organic cotton in some arrangements. This can be accomplished, for example, by way of the process detailed below in FIGS. 3A-3B.

At following process step 206, the absorbent body can be enclosed within a protective sleeve. This can include enclosing the absorbent body within a protective sleeve at the exterior surface, interior surface, and both distal ends of the absorbent body. The protective sleeve can be porous to allow fluid to enter the absorbent body but prevent absorbent body material from passing through the protective sleeve, and the absorbent body and protective sleeve combine to define an overall tubular structure having an inner hollow region and a first diameter. This can be accomplished, for example, by way of the processes detailed below in FIGS. 3C-3D and 4A-4E.

At the next process step 208, a string can be coupled to the protective sleeve. The string can be used as a removal feature during use of the finished tampon product. In various arrangements, coupling the string to the protective sleeve can include punching an end of the string through a top outer surface of the protective sleeve, pushing the string through the protective sleeve, a top portion of the absorbent body, an inner surface of the protective sleeve, the hollow region, another inner surface of the protective sleeve, a bottom portion of the absorbent body, and out from a bottom outer surface of the protective sleeve, and then coupling the end of the string to a remaining portion of the string that has not passed through the protective sleeve. The string may or may not help to hold the protective sleeve in place against the absorbent body, and the string may or may not help to hold shut a compressed back distal end of the overall structure. In some embodiments stitching may be added to the protective sleeve to accomplish one or both of these functions, as detailed below.

At subsequent process step 210, the overall structure can be compressed. This can involve a primary compression phase that involves laterally compressing the product to create a more compressed and uniform elongated lateral shape and/or a secondary compression phase that involves applying an axial compression force to compress the product to a desired length. This can be accomplished, for example, by way of the processes detailed below in FIGS. 10A-10C.

At the next optional process step 212, a coating can be applied to the outer surface of the finished tampon product. This can be, for example, a coating that serve as a pain reducer. In some arrangements, the optional coating can include a cannabidiol oil component. This can be accomplished, for example, by way of the process detailed below in FIG. 10D.

At the following optional process step 214, the finished tampon product can be inserted into an applicator. This can involve inserting the finished tampon product into an applicator, and then inserting a plunger into the applicator. The tampon string can extend out the back end of the applicator and may travel through a hollow interior of a plunger shaft. This can be accomplished, for example, by way of the processes detailed below in FIGS. 10E-10F. The method then ends at end step 216.

Figure 3A:
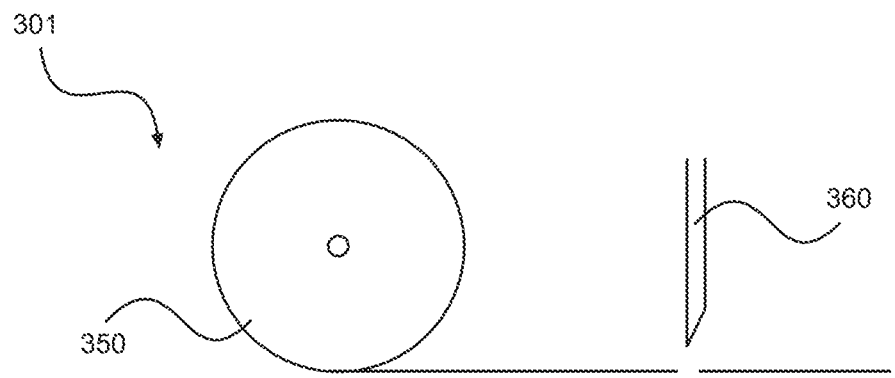
FIG. 3A illustrates in diagrammatic view a process step of cutting an absorbent body according to one embodiment of the present disclosure.
Figure 3A:
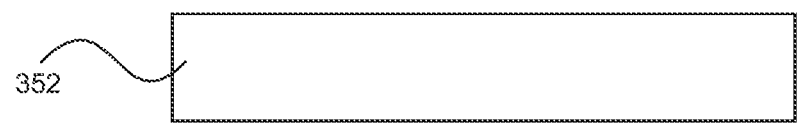

Starting with FIGS. 3A-3D, the start of an overall tampon manufacturing process is shown in a series of progressing diagrammatic views. FIG. 3A illustrates in diagrammatic view 301 a process step of cutting an absorbent body. Absorbent body material source 350 can include material that forms the bulk of absorbent material in a final tampon product. Such material can be, for example, natural organic cotton, which may be layered in a large industrial roll. In some arrangements, hemp mixed with natural organic cotton may also be used. Other natural fibrous materials are also contemplated for absorbent body material source 350. A cutter 360 can be used to cut unrolled material from absorbent body material source 350 into an absorbent material layer 352 of desired dimensions, such as a specific thickness, length and width. Operations of unrolling material from the absorbent body material source 350 and cutting the material to the desired dimensions can be automated, such as by standard industrial manufacturing processes using robotically controlled equipment.

Figure 3B:
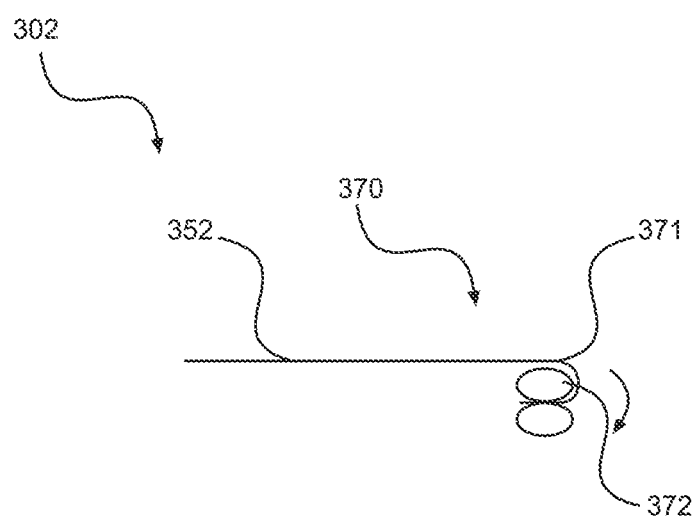
FIG. 3B illustrates in diagrammatic view a process step of rolling the cut absorbent body around machine prongs according to one embodiment of the present disclosure.
Figure 3B:
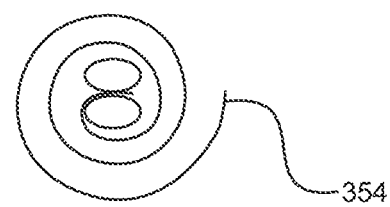

FIG. 3B illustrates in diagrammatic view 302 a process step of rolling the cut absorbent body material around machine prongs. As shown, an end of absorbent material layer 352 can be pinched between a first set of machine prongs 370, which can include individual prongs 371, 372. These prongs 371, 372 can be formed from any suitable manufacturing material, such as, for example, a medical grade metal or other material. The first set of machine prongs 370 can then be rotated such that a rolled absorbent material 354 is formed around the prongs. Prongs 371, 372 can be dimensioned such that an appropriately sized internal hollow region is formed in the center of the rolled absorbent material 354 when the prongs are removed therefrom. Alternatively, a single rod can be used in lieu of a set of machine prongs 370 for rolling the cut absorbent body.

Figure 3C:
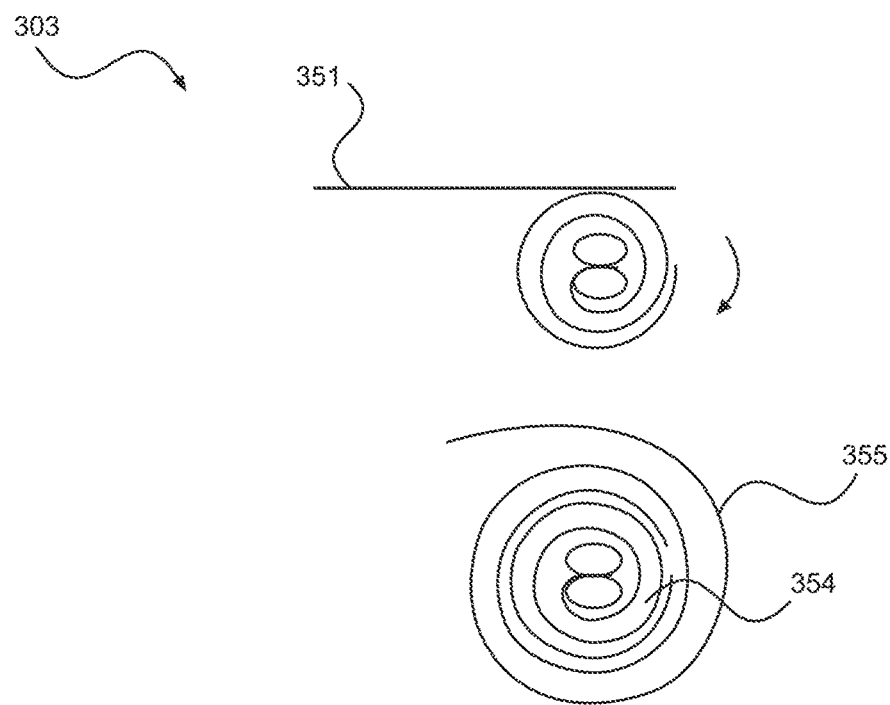
FIG. 3C illustrates in diagrammatic view a process step of rolling a porous sheet around the rolled absorbent body according to one embodiment of the present disclosure.

FIG. 3C illustrates in diagrammatic view 303 a process step of rolling a porous sheet around the rolled absorbent body. Porous sheet material source 351 can provide a porous sheet material that is then rolled around the rolled absorbent material 354. This can also be accomplished by rotating the first set of machine prongs as the porous sheet material is placed against the rolled absorbent material 354, which can result in a rolled porous sheet material 355 being formed around the rolled absorbent material. The porous sheet material can be, for example, a nonwoven natural organic cotton that has been pressure treated for strength, and the porous sheet can have a thickness of about 4 mils. Other materials and thicknesses are also possible. In particular, the rolled porous sheet material 355 can form a protective sleeve that allows fluid to pass therethrough to enter the rolled absorbent material 354 but prevents fiber and other absorbent body material from passing through the protective sleeve.

Figure 3D:
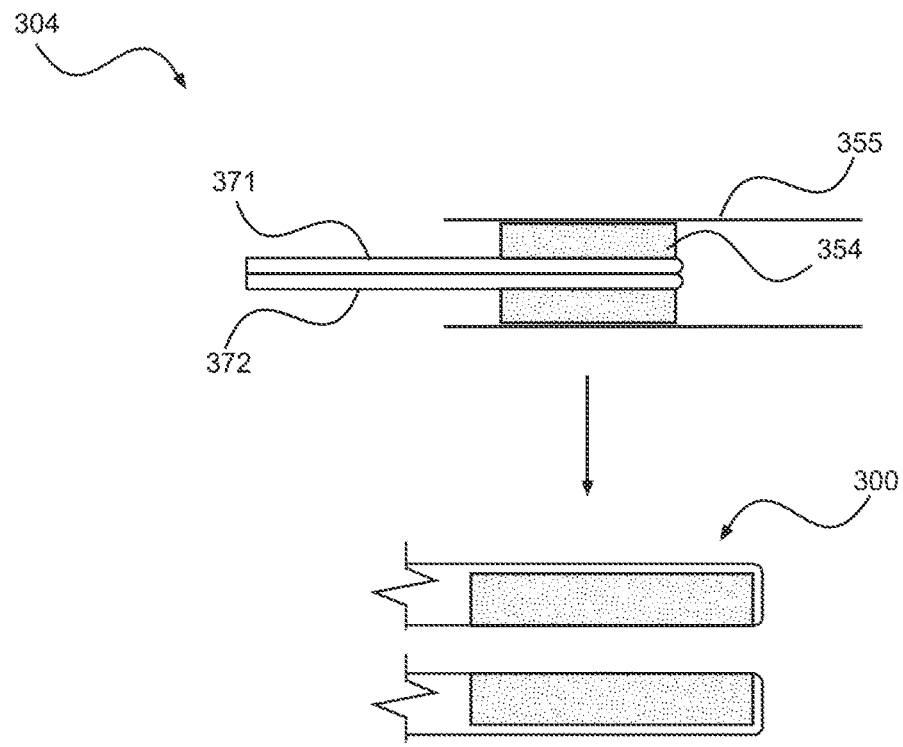
FIG. 3D illustrates in diagrammatic view a process step of enclosing the absorbent body within the porous sheet according to one embodiment of the present disclosure.

FIG. 3D illustrates in diagrammatic view 304 a process step of enclosing the absorbent body within the porous sheet. While diagrammatic view 303 above is shown from an end cross-section view, diagrammatic view 304 of FIG. 3D depicts the same arrangement from a side cross-section view. Again, a rolled absorbent material 354 has been formed around machine prongs 371, 372, and a rolled porous sheet material 355 has been formed around the rolled absorbent material 354. As shown, the rolled porous sheet material 355 can have a length that is significantly longer than the length of the rolled absorbent material 354. In various arrangements, the rolled porous sheet material 355 can extend past both distal ends of the rolled absorbent material 354 a distance that exceeds the length and half the height of the rolled absorbent material 354. This excess rolled porous sheet material 355 can then be manipulated to fully encapsulate the rolled absorbent material 354 at all surfaces to arrive at partially formed tubular shaped tampon 300.

Figure 4A:
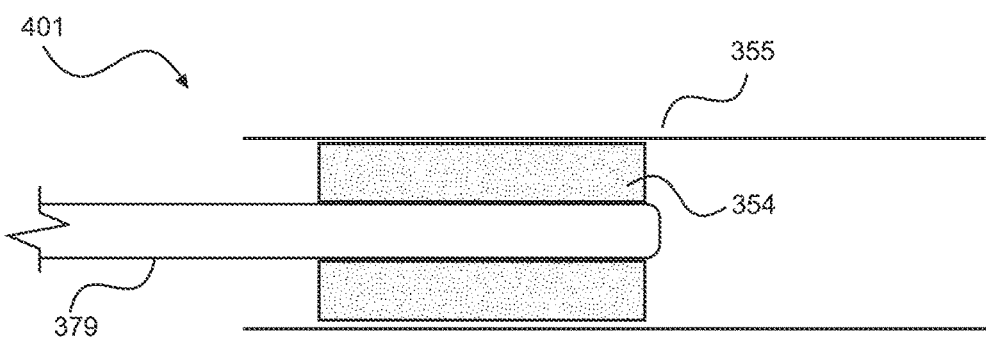
FIG. 4A illustrates in diagrammatic view a subprocess step of beginning to enclose an absorbent body wrapped around an elongated rod within a porous sheet according to one embodiment of the present disclosure.

The process shown in FIG. 3D is expanded in FIGS. 4A-4E, which provide a detailed breakdown of one way of enclosing the absorbent body within the porous sheet in a series of progressing diagrammatic views. FIG. 4A illustrates in diagrammatic view 401 a subprocess step of beginning to enclose an absorbent body wrapped around an elongated rod within a porous sheet. FIG. 4A can correlate to the first portion of FIG. 3D above, with a porous sheet material 355 rolled around an absorbent material 354, which is in turn can be rolled around machine prongs or alternatively an elongated rod 379. Again, the length of porous sheet material 355 can be substantially greater than the length of absorbent material 354, with the ends of the porous sheet material 355 extending significantly beyond both distal ends of the absorbent material 354. In one non-limiting example for purposes of illustration, the length of absorbent material 354 can be about 5 cm and the length of porous sheet material 355 can be about 14 cm, and porous sheet material 355 can be arranged such that it extends past the absorbent material by 2 cm on a back end thereof and by 7 cm on a front end thereof.

Figure 4B:
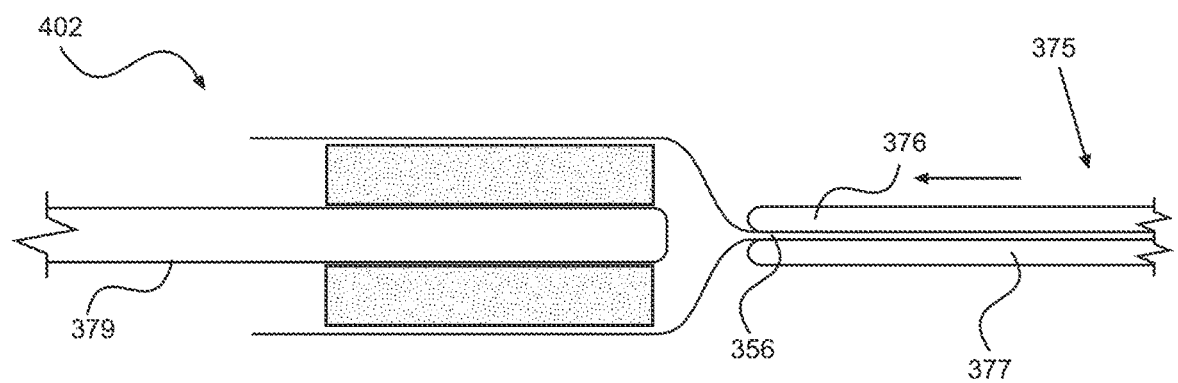
FIG. 4B illustrates in diagrammatic view a subprocess step of pinching closed a first distal end of the porous sheet with a set of machine prongs according to one embodiment of the present disclosure.

FIG. 4B illustrates in diagrammatic view 402 a subprocess step of pinching closed a first distal end of the porous sheet with a set of machine prongs. Set of machine prongs 375, which can include prongs 376, 377, can be used to pinch together one end of the porous sheet material 355 that extends past a front distal end of the absorbent material 354 to form pinched porous sheet end 356. Set of machine prongs 375 can be formed from a medical grade metal or other material.

Figure 4C:
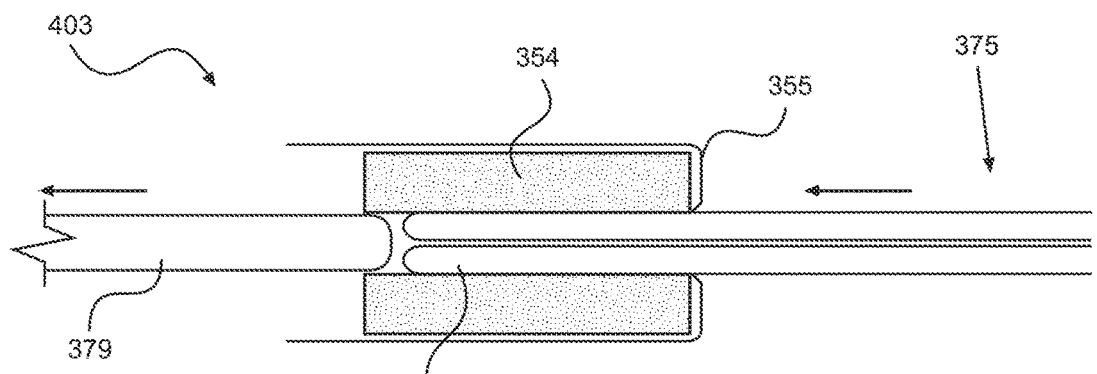
FIG. 4C illustrates in diagrammatic view subprocess steps of removing the elongated rod and pushing the pinched closed distal end of the porous sheet into the hollow region of the absorbent body with the set of machine prongs according to one embodiment of the present disclosure.

FIG. 4C illustrates in diagrammatic view 403 subprocess steps of removing the elongated rod and pushing the pinched closed distal end of the porous sheet into the hollow region of the absorbent body with the set of machine prongs. Elongated rod 379 can be removed from the hollow interior region of absorbent material 354, and set of machine prongs 375 can then be inserted into the hollow region while still holding together pinched porous sheet end 356. This can result in porous sheet material 355 wrapping around from the top and bottom of the absorbent material 354 to cover the front distal end of the absorbent material 354 and also the inner surfaces of the absorbent material 354 along the hollow interior region.

Figure 4D:
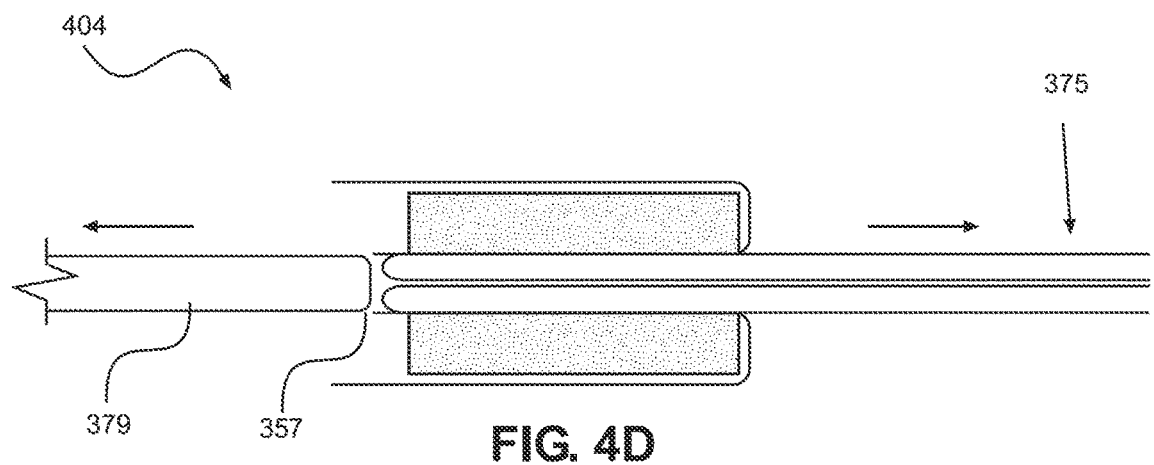
FIG. 4D illustrates in diagrammatic view a subprocess step of pushing the pinched closed first distal end of the porous sheet fully through the hollow region and past the opposite distal end of the absorbent body according to one embodiment of the present disclosure.

FIG. 4D illustrates in diagrammatic view 404 a subprocess step of pushing the pinched closed first distal end of the porous sheet fully through the hollow region and past the opposite distal end of the absorbent body. As set of machine prongs 375 extends fully through the internal hollow region of the bulk absorbent material, the porous sheet can fully line the interior surfaces of the internal hollow region. Upon full extension, the distal end of the porous sheet can be released from set of machine prongs 375 to become unpinched together porous sheet end 357, which can extend past the back distal end of the bulk absorbent material. Set of machine prongs 375 can open slightly to facilitate this release, or the porous sheet can simply slide out from the grasp of the machine prongs due to the porous sheet being fully extended.

Figure 4E:
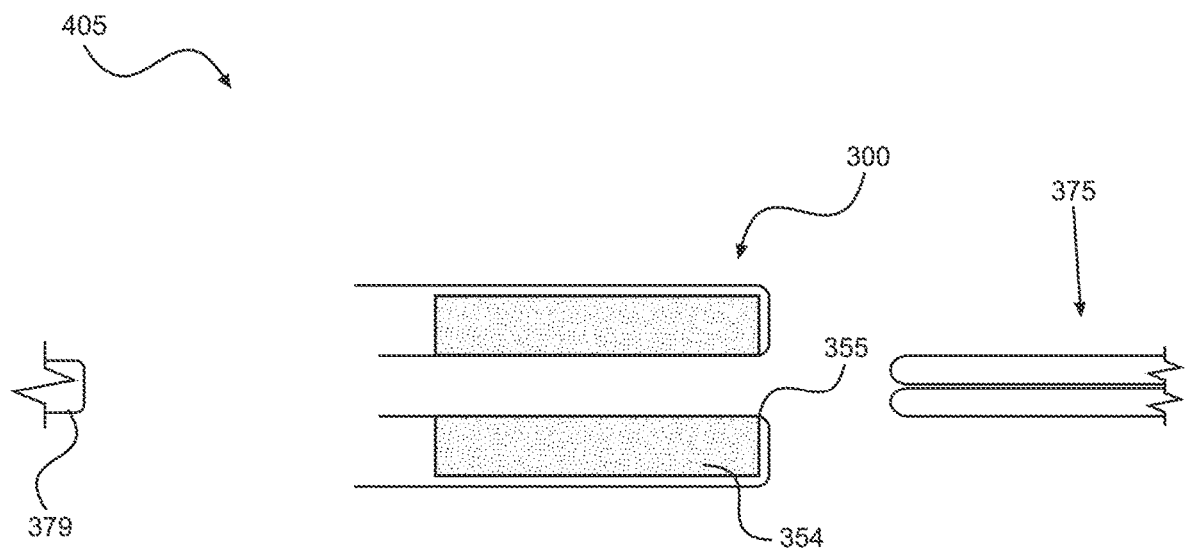
FIG. 4E illustrates in diagrammatic view a subprocess step of fully removing the elongated rod and set of machine prongs according to one embodiment of the present disclosure.
Figure 5A:
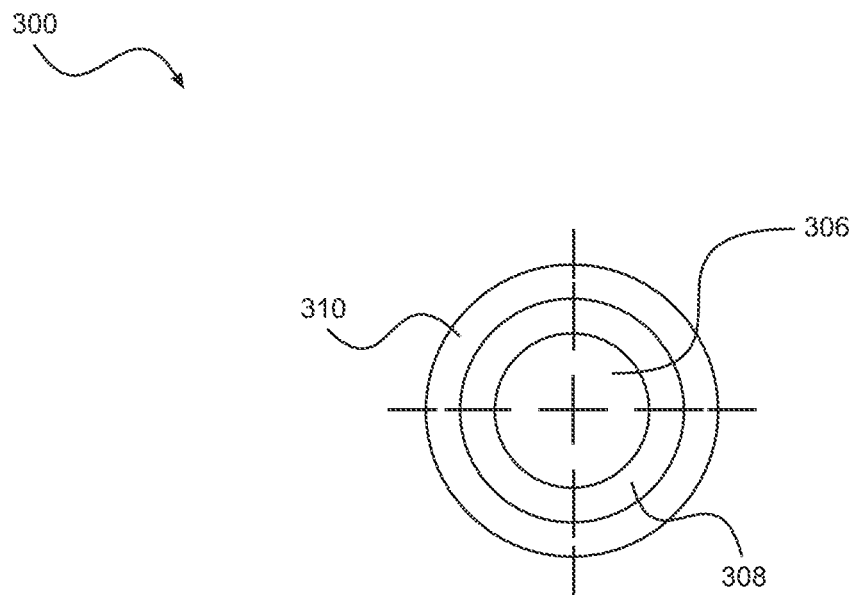
FIG. 5A illustrates in front elevation view an example partially formed tubular shaped tampon prior to string coupling and compression according to one embodiment of the present disclosure.
Figure 5B:
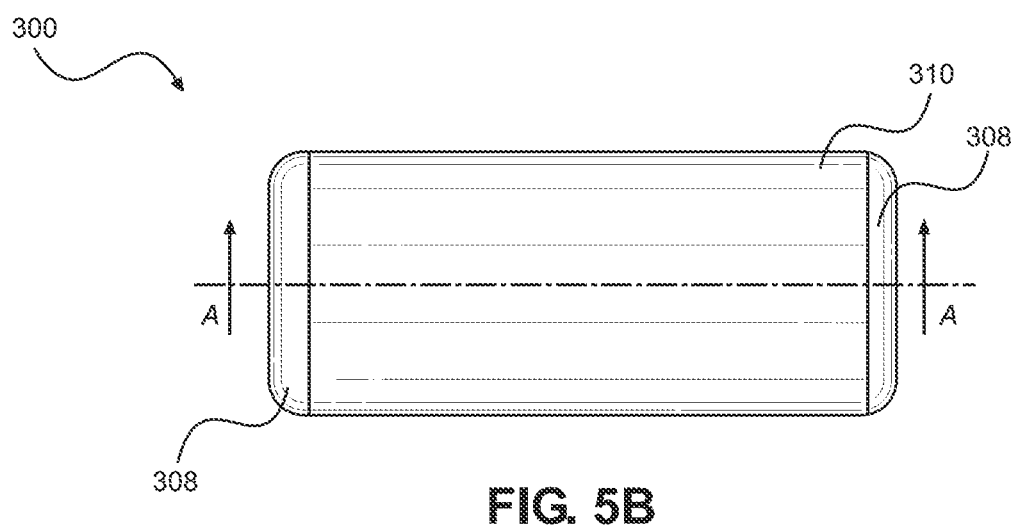
FIG. 5B illustrates in side elevation view the example partially formed tubular shaped tampon of FIG. 5A according to one embodiment of the present disclosure.
Figure 5C:
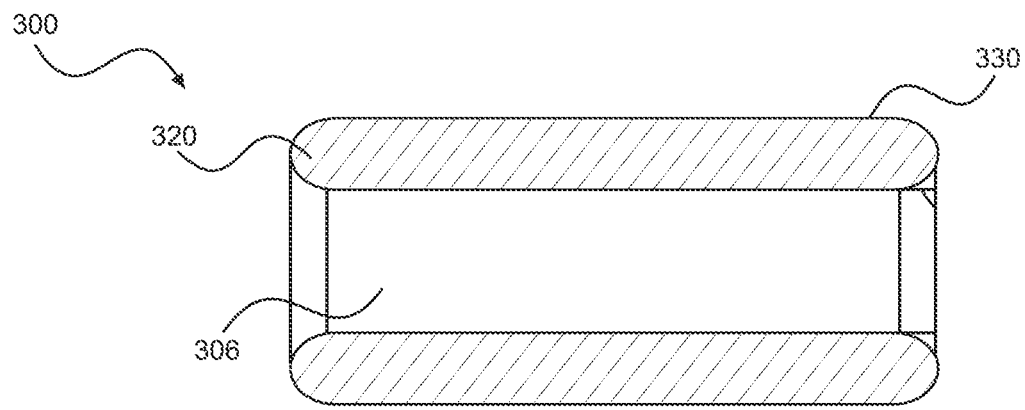
FIG. 5C illustrates in top cross-section view the example partially formed tubular shaped tampon of FIG. 5A according to one embodiment of the present disclosure.
Figure 5D:
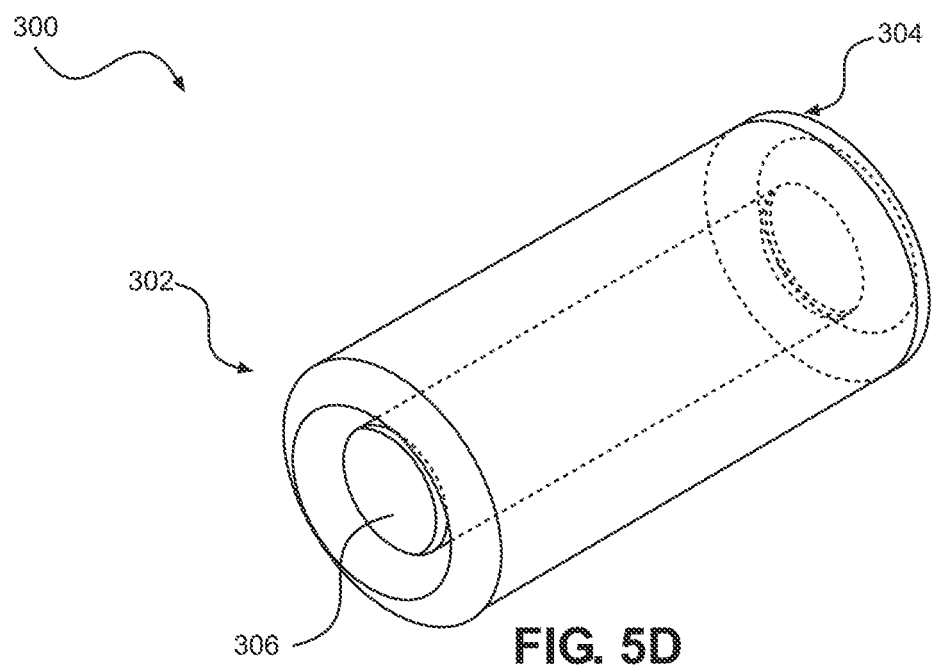
FIG. 5D illustrates in side perspective view the example partially formed tubular shaped tampon of FIG. 5A according to one embodiment of the present disclosure.

FIG. 4E illustrates in diagrammatic view 405 a subprocess step of fully removing the elongated rod and set of machine prongs. Elongated rod 379 can be fully removed from both the bulk absorbent material and the extended back distal end of porous sheet 355 and set of machine prongs 375 can also be removed from the internal hollow region of the bulk absorbent material. This can then result in partially formed tubular shaped tampon 300, which can also be referred to as a "blank."

Moving next to FIGS. 5A-5D, an example partially formed tubular shaped tampon prior to string coupling and compression is shown in front elevation, side elevation, top cross-section, and side perspective views respectively. Partially formed tubular shaped tampon 300, which again can be referred to as a "blank," can represent the foregoing finished tampon 100 at an intermediate stage of the manufacturing process. In particular, partially formed tubular shaped tampon 300 can represent the "blank" structure formed by the processes detailed in FIGS. 3A through 4E above. Partially formed tubular shaped tampon 300 can be an overall tubular structure 310 that includes absorbent body 320 surrounded by protective sleeve 330. Partially formed tubular shaped tampon 300 can also include an inner hollow region 306 and tapered regions 308 at front distal end 302 and back distal end 304. While the loose distal ends of protective sleeve 330 are shown in FIG. 4E (i.e., ends of porous sheet 355), these have not been shown in FIGS. 5A-5D for purposes of simplicity in illustration.

Figure 6:
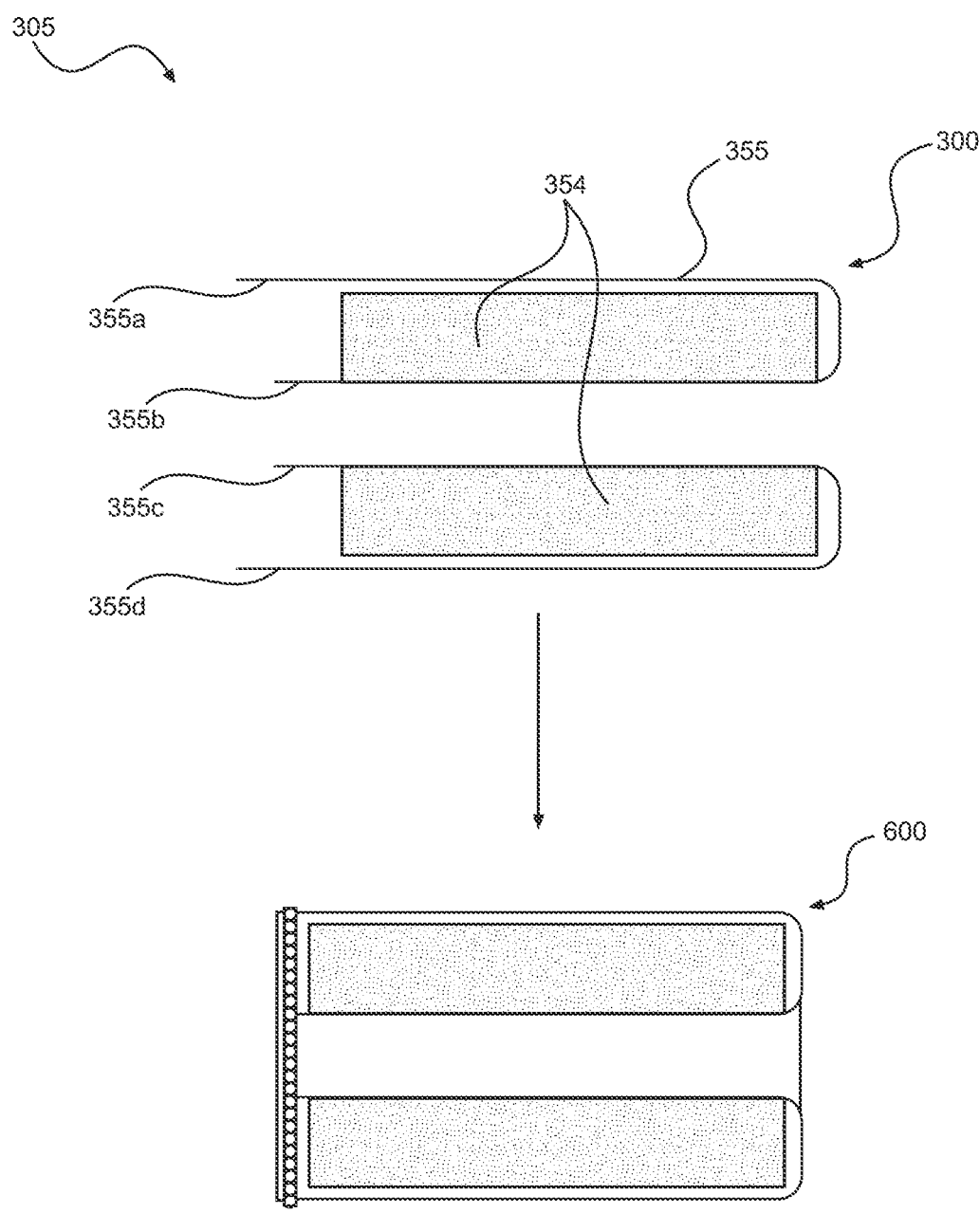
FIG. 6 illustrates in diagrammatic view a process step of stitching together the ends of the porous sheet according to one embodiment of the present disclosure.
Figure 7A:
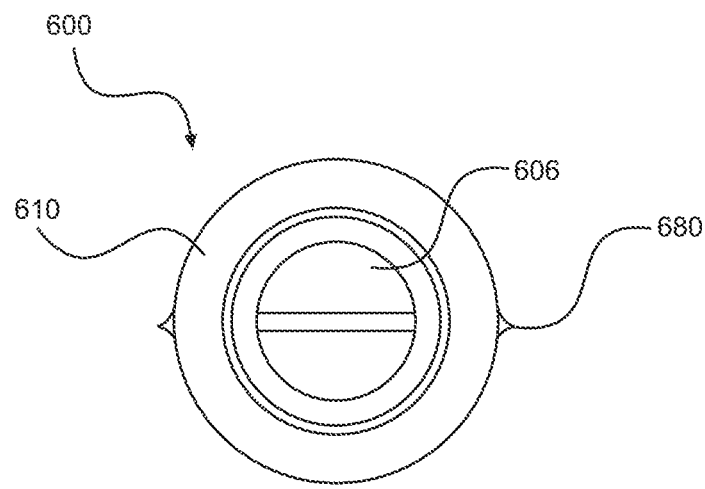
FIG. 7A illustrates in front elevation view an example partially formed and stitched tubular shaped tampon prior to string coupling and compression according to one embodiment of the present disclosure.
Figure 7B:
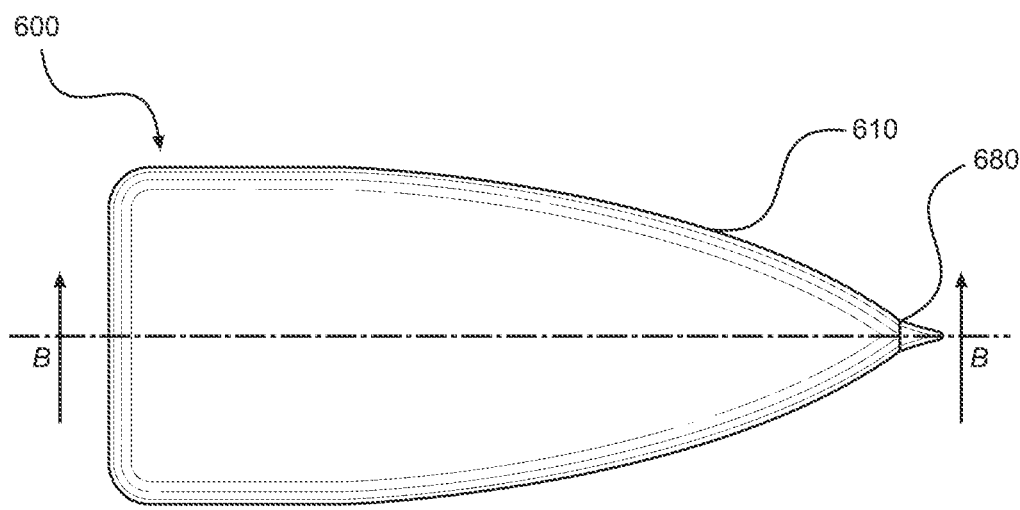
FIG. 7B illustrates in side elevation view the example partially formed and stitched tubular shaped tampon of FIG. 7A according to one embodiment of the present disclosure.
Figure 7C:
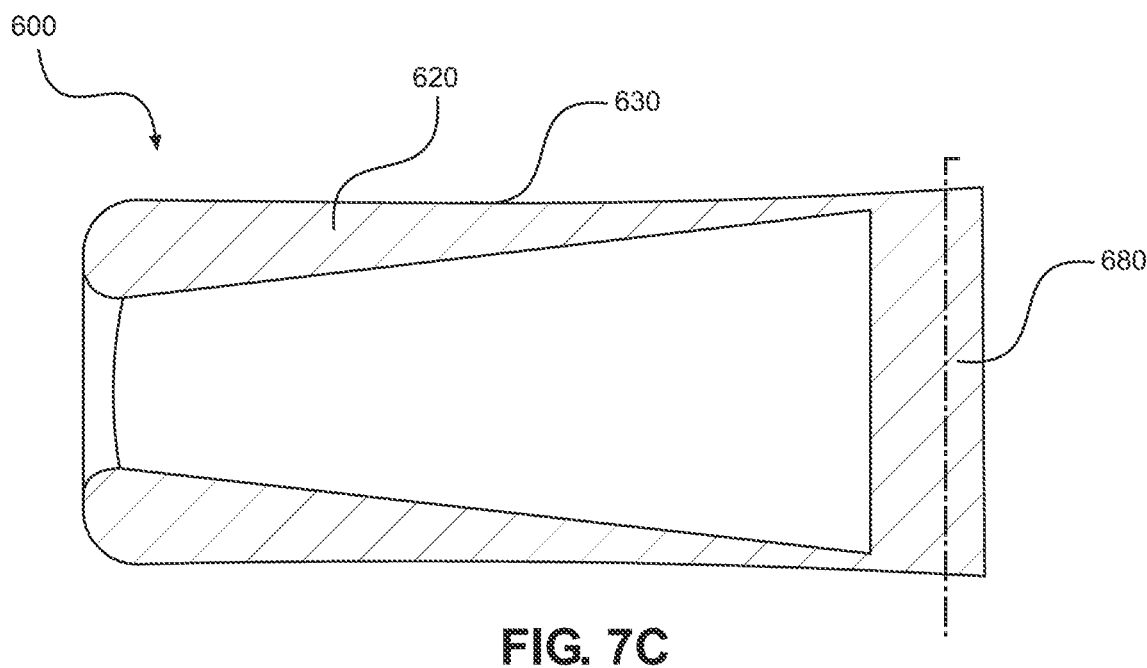
FIG. 7C illustrates in top cross-section view the example partially formed and stitched tubular shaped tampon of FIG. 7A according to one embodiment of the present disclosure.
Figure 7D:
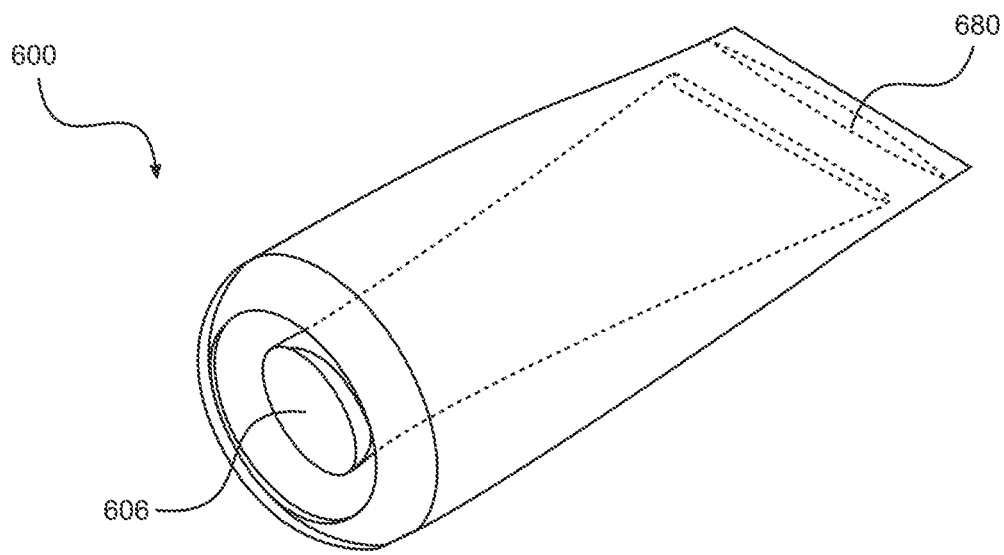
FIG. 7D illustrates in side perspective view the example partially formed and stitched tubular shaped tampon of FIG. 5A according to one embodiment of the present disclosure.

FIG. 6 illustrates in diagrammatic view a process step 305 of stitching together the ends of the porous sheet. Partially formed tubular shaped tampon 300 can have loose distal ends 355a, 355b, 355c, 355d of porous sheet material 355, which loose distal ends all extend past the back distal end of the absorbent material 354 after the processes detailed in FIGS. 4A-4E. In order to completely enclose and lock in the tubular shaped absorbent material 354, loose distal ends 355a, 355b, 355c, 355d can all be stitched together, such as by stitching 680.

Partially formed and stitched tubular shaped tampon 600 can be formed by taking partially formed tubular shaped tampon 300, pinching or compressing shut the back distal end where loose distal ends 355a, 355b, 355c, 355d extend past the absorbent material, and applying stitching 680 to hold the back distal end shut. Stitching 680 can be an chain stitch, for example, which can be applied using any suitable automated manufacturing stitching process. Excess porous sheet material beyond stitching 680 can then be trimmed away. In various embodiments, stitching 680 can be formed from an organic cotton material. Partially formed and stitched tubular shaped tampon 600 then forms an overall cupped shape where the front distal end can be inserted such that fluids can flow into the internal cavity and expand the tampon more uniformly during use.

Continuing with FIGS. 7A-7D, an example partially formed and stitched tubular shaped tampon prior to string coupling and compression is shown in front elevation, side elevation, top cross-section, and side perspective views respectively. Partially formed stitched tubular shaped tampon 600 can represent the foregoing finished tampon 100 at another intermediate stage of the manufacturing process that is further along than partially formed tubular shaped tampon 300 above. In particular, partially formed stitched tubular shaped tampon 600 can represent the stitched structure formed by the process set forth in FIG. 6 above. Partially formed stitched tubular shaped tampon 600 can be an overall cupped tubular structure 610 that includes absorbent body 620 surrounded by protective sleeve 630. Partially formed stitched tubular shaped tampon 600 can also include an inner hollow region 606 and a back distal end that has been pinched together and stitched shut with stitching 680.

Figure 8:
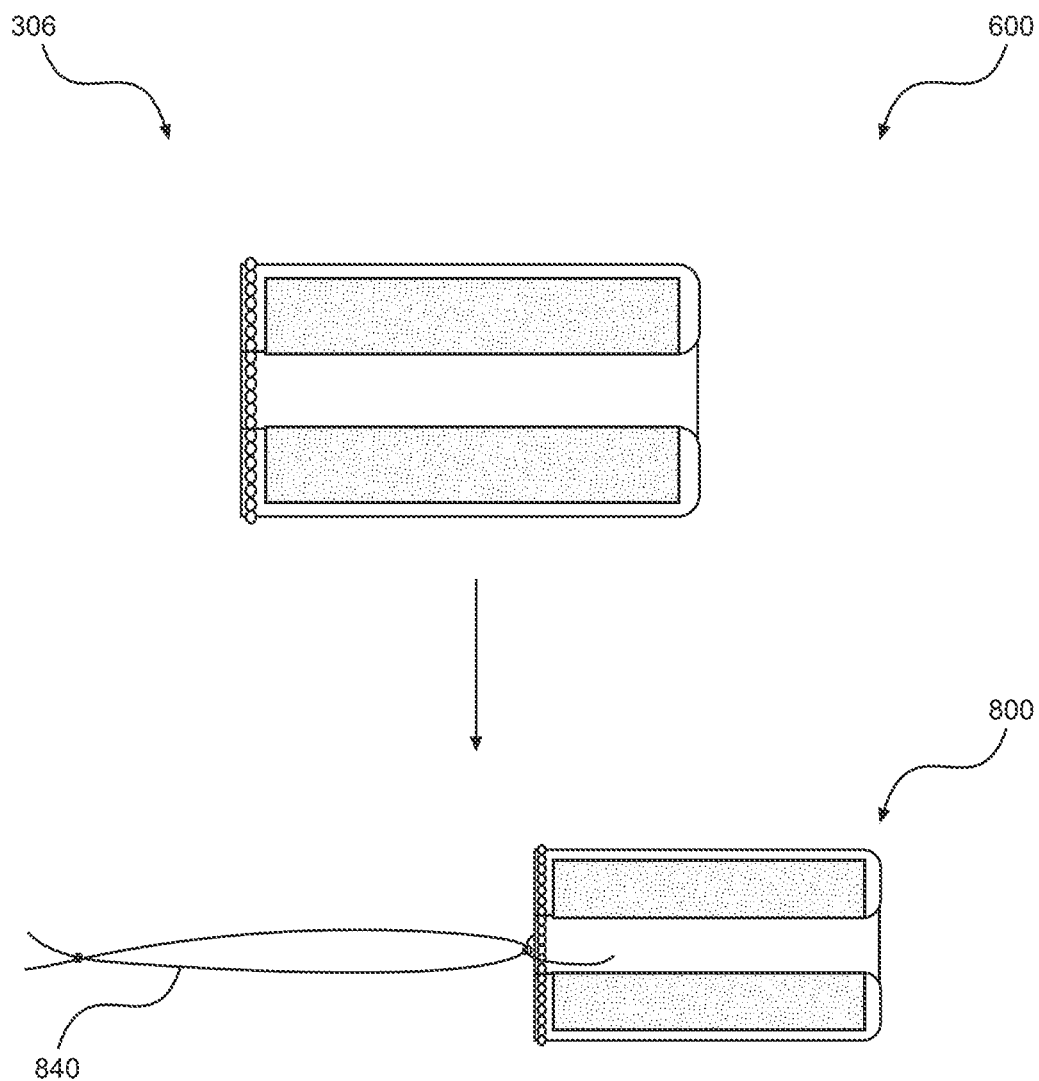
FIG. 8 illustrates in diagrammatic view a process step of coupling a string to the absorbent body and porous sheet according to one embodiment of the present disclosure.

FIG. 8 illustrates in diagrammatic view a process step of coupling a string to the absorbent body and porous sheet. As noted above, partially formed stitched tubular shaped tampon 600 can be pinched shut at its back end as part of the stitching process to fully enclose the absorbent material within the protective sleeve. String 840 can then be punched through all layers of the compressed back distal end and coupled to itself to arrive at partially formed, stitched, and string coupled tubular shaped tampon 800. String 840 can be coupled in a variety of different ways. In some embodiments, string 840 can be attached by needle punching string 840 through a top hole in the protective sleeve and pushing the string through all materials until it exits at a bottom hole in the protective sleeve. This can involve pushing the string through a top outer surface of the protective sleeve, a top portion of the absorbent body, an inner surface of the protective sleeve, the hollow region, another inner surface of the protective sleeve, a bottom portion of the absorbent body, and out from a bottom outer surface of the protective sleeve.

Figure 9A:
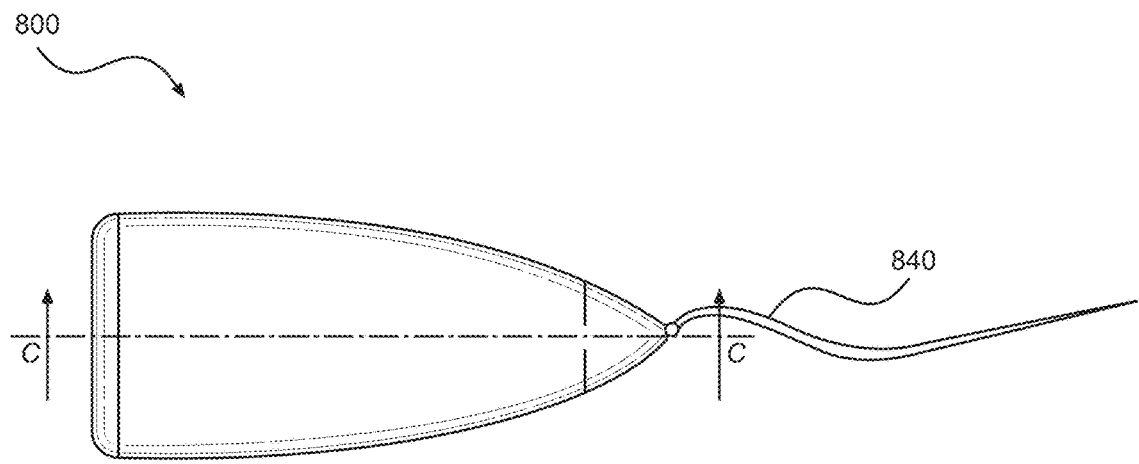
FIG. 9A illustrates in side elevation view an example partially formed, stitched, and string coupled tubular shaped tampon prior to compression according to one embodiment of the present disclosure.
Figure 9B:
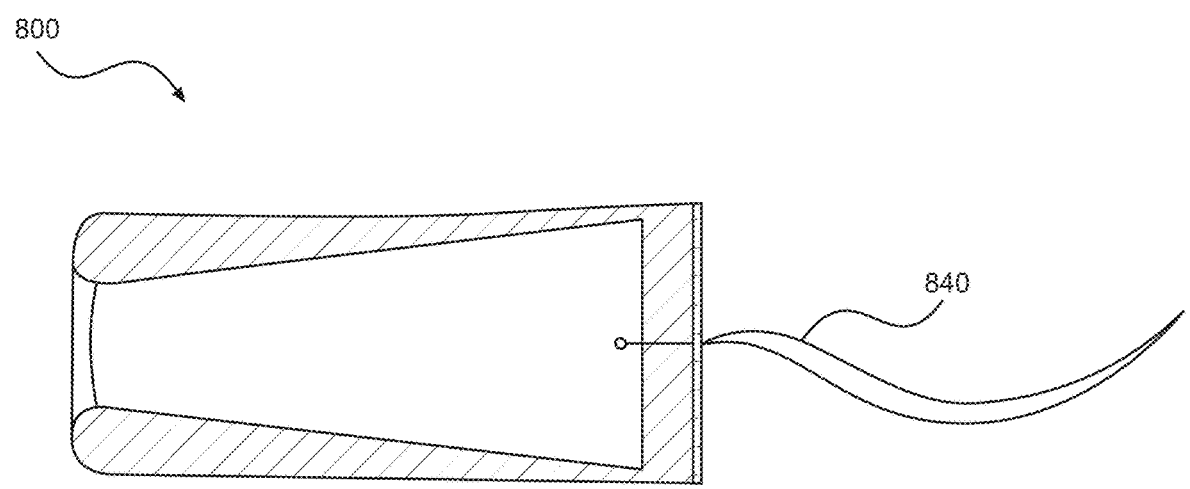
FIG. 9B illustrates in top cross-section view the example partially formed, stitched, and string coupled tubular shaped tampon of FIG. 9A according to one embodiment of the present disclosure.

FIGS. 9A and 9B illustrates in side elevation and top cross-section views respectively an example partially formed, stitched, and string coupled tubular shaped tampon prior to compression. In various arrangements, the exiting end of string 840 can be coupled to a remaining portion of the string that has not passed through the protective sleeve. This can involve, for example, passing the end of the string 840 through a loop in the remaining portion of the string. Alternatively, the end of the string 840 can form a loop or a knot on the remaining portion of the string. Still further, a clamp or wrap can be used to hold the end of string 840 against the remaining portion of string. Other ways of affixing or coupling the string 840 to hold it in place are also possible, as will be readily appreciated.

Figure 10A:
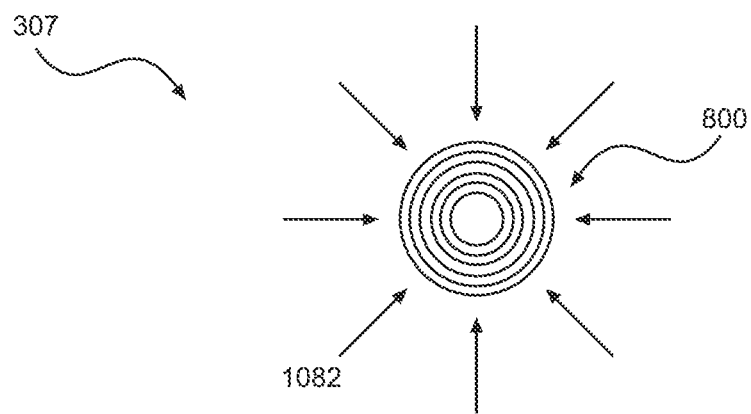
FIG. 10A illustrates in diagrammatic view a process step of primary compressing the absorbent body and porous sheet according to one embodiment of the present disclosure.

Transitioning back to FIGS. 10A-10F, remaining process steps for forming a finished tampon product will now be described. FIG. 10A illustrates in diagrammatic view 307 a process step of primary compressing the absorbent body and porous sheet. Partially formed, stitched, and string coupled tubular shaped tampon 800 can be compressed at a primary compression stage to create a more compact and uniform elongated lateral shape. A lateral precompression force 1082 can be applied along all lateral exterior surfaces to arrive at an overall cylindrical shape having a diameter that is less than the diameter of partially formed, stitched, and string coupled tubular shaped tampon 800. In various arrangements, this reduced diameter can be sufficient to place the resulting partially formed tampon product into an axial compressor for a secondary compression stage.

Figure 10B:
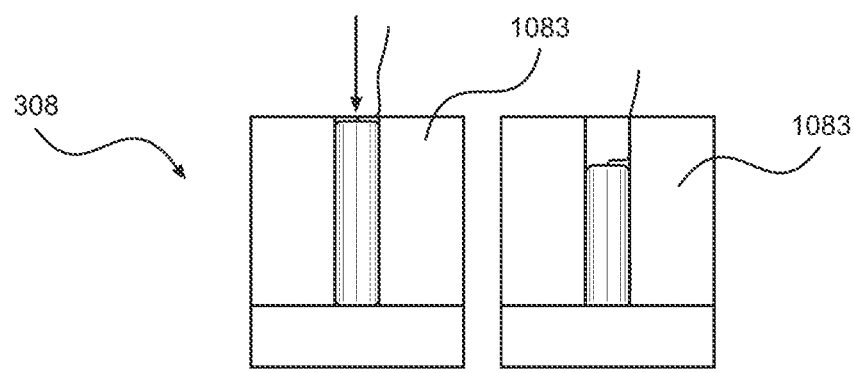
FIG. 10B illustrates in diagrammatic view a process step of secondary compressing the absorbent body and porous sheet according to one embodiment of the present disclosure.

FIG. 10B illustrates in diagrammatic view 308 a process step of secondary compressing the absorbent body and porous sheet in a compressor to form a finished tampon product. Compressor 1083 can have an internal cavity that is sized and shaped to contain the primary compressed partially formed tampon product formed above. After insertion into the cavity of compressor 1083, an axial compression force can be applied to compress the partially formed tampon product to a desired length, resulting in a finished tampon product having a desired length and diameter.

Figure 10C:
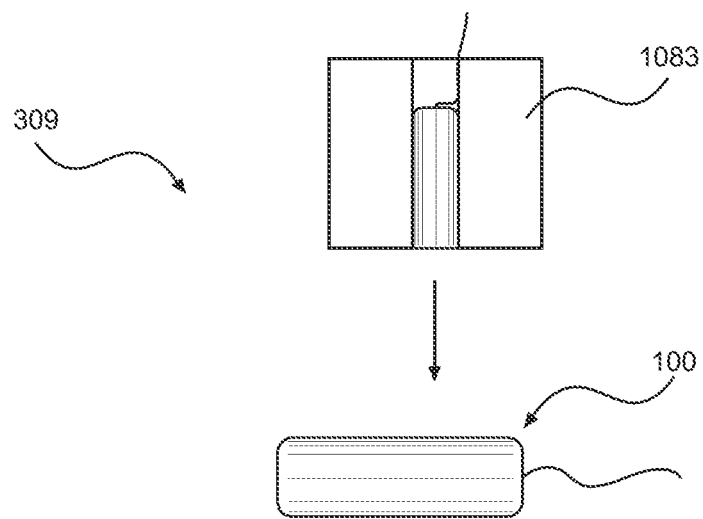
FIG. 10C illustrates in diagrammatic view a process step of extracting the absorbent body and porous sheet from a compressor according to one embodiment of the present disclosure.

FIG. 10C illustrates in diagrammatic view 309 a process step of extracting the absorbent body and porous sheet from a compressor. Finished tampon product 100 can then be extracted from the internal cavity of compressor 1083 and may then be ready for packaging or use. Alternatively, further optional steps may be taken with respect to finished tampon product 100. In some embodiments, a "regular" sized finished tampon product 100 can have a ribbon length of about 140-160 mm, a ribbon width of about 50 mm, a nonwoven length of about 100-120 mm, a nonwoven width of about 140 mm, and a post-compression diameter of about 14-16 mm (with a pre-compression diameter of about 21.5-23.5 mm). In other embodiments, a "super" sized finished tampon product 100 can have a ribbon length of about 220-260 mm, a ribbon width of about 50 mm, a nonwoven length of about 110-150 mm, a nonwoven width of about 140 mm, and a post-compression diameter of about 10-12 mm (with a pre-compression diameter of about 24-26 mm). Other sizes and dimensions are also possible, and it will be readily appreciated that the examples provided here for purposes of illustration are not limiting in any way with respect to the sizes and dimensions that finished tampon product 100 can have.

Figure 10D:
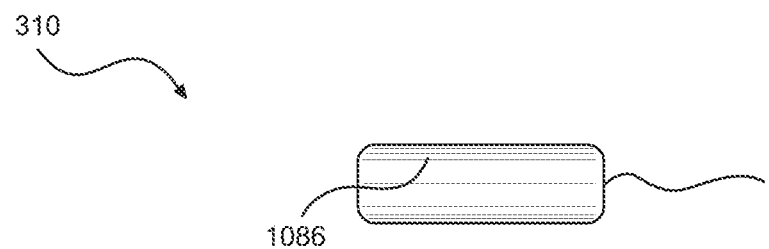
FIG. 10D illustrates in diagrammatic view a process step of applying a coating to the outer surface of the porous sheet according to one embodiment of the present disclosure.

FIG. 10D illustrates in diagrammatic view 310 an optional process step of applying a coating to the outer surface of the porous sheet. Optionally, a coater may be used to apply a coating 1086 to the outer surface of the porous sheet, and thus the exterior surface of the finished tampon product. Such an optional coating can be, for example, a coating that can include a cannabidiol oil, which can increase pain relief during tampon use.

Figure 10E:
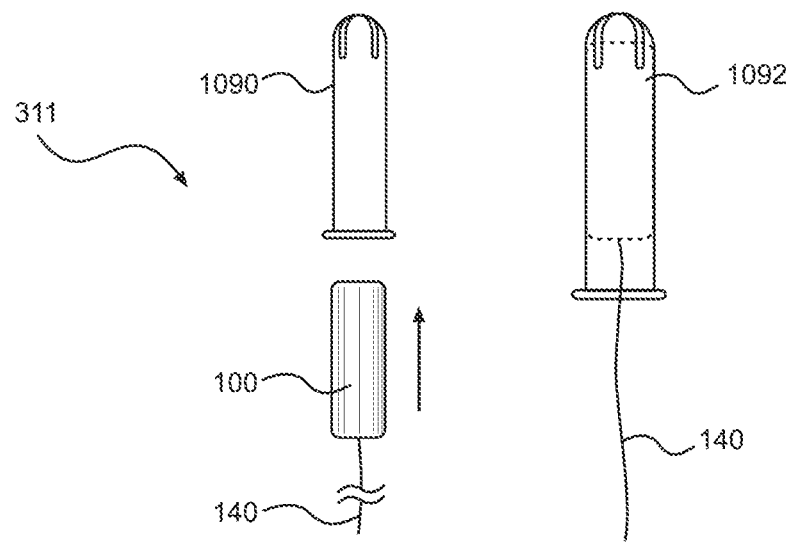
FIG. 10E illustrates in diagrammatic view a process step of inserting a finished tubular shaped tampon into an applicator according to one embodiment of the present disclosure.

FIG. 10E illustrates in diagrammatic view 311 an optional process step of inserting a finished tubular shaped tampon into an applicator. Finished tampon product 100, which may or may not have a coating, can be inserted into applicator 1090 to form tampon applicator combination 1092.

Figure 10F:
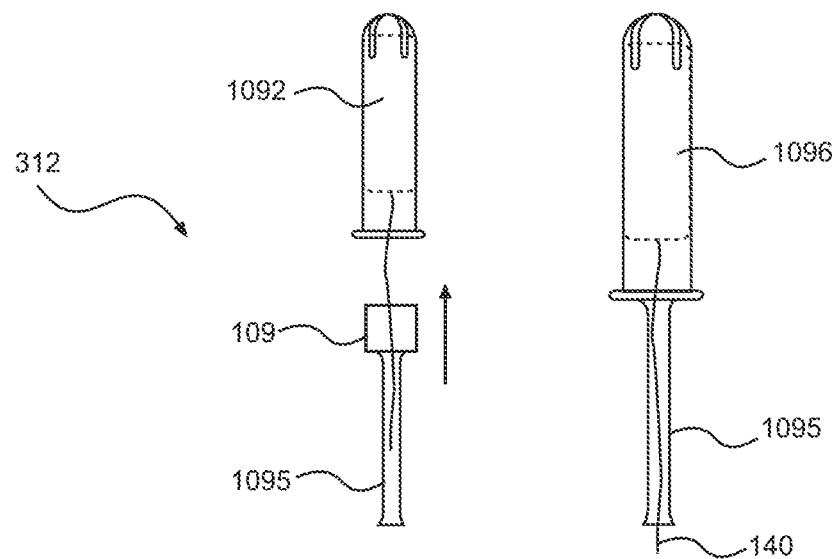
FIG. 10F illustrates in diagrammatic view a process step of inserting a plunger into the applicator according to one embodiment of the present disclosure.

FIG. 10F illustrates in diagrammatic view 312 an optional process step of inserting a plunger into the applicator to form a finished tampon and applicator product. An applicator plunger 1094 can be inserted into the tampon applicator combination 1092 to form tampon applicator plunger combination 1096. As will be readily appreciated, the tampon product can be arranged such that the string extends out the back end of the applicator and may travel through a hollow interior of plunger shaft 1095.

For each of the foregoing process and subprocess steps in FIGS. 3A-3D, 4A-4E, 6, 8, and 10A-10F, it will be readily appreciated that some or all steps may be performed automatically using suitable manufacturing machinery and production techniques. Various manufacturing components can be robotic and can be operated through the use of appropriate software.

Figure 11:
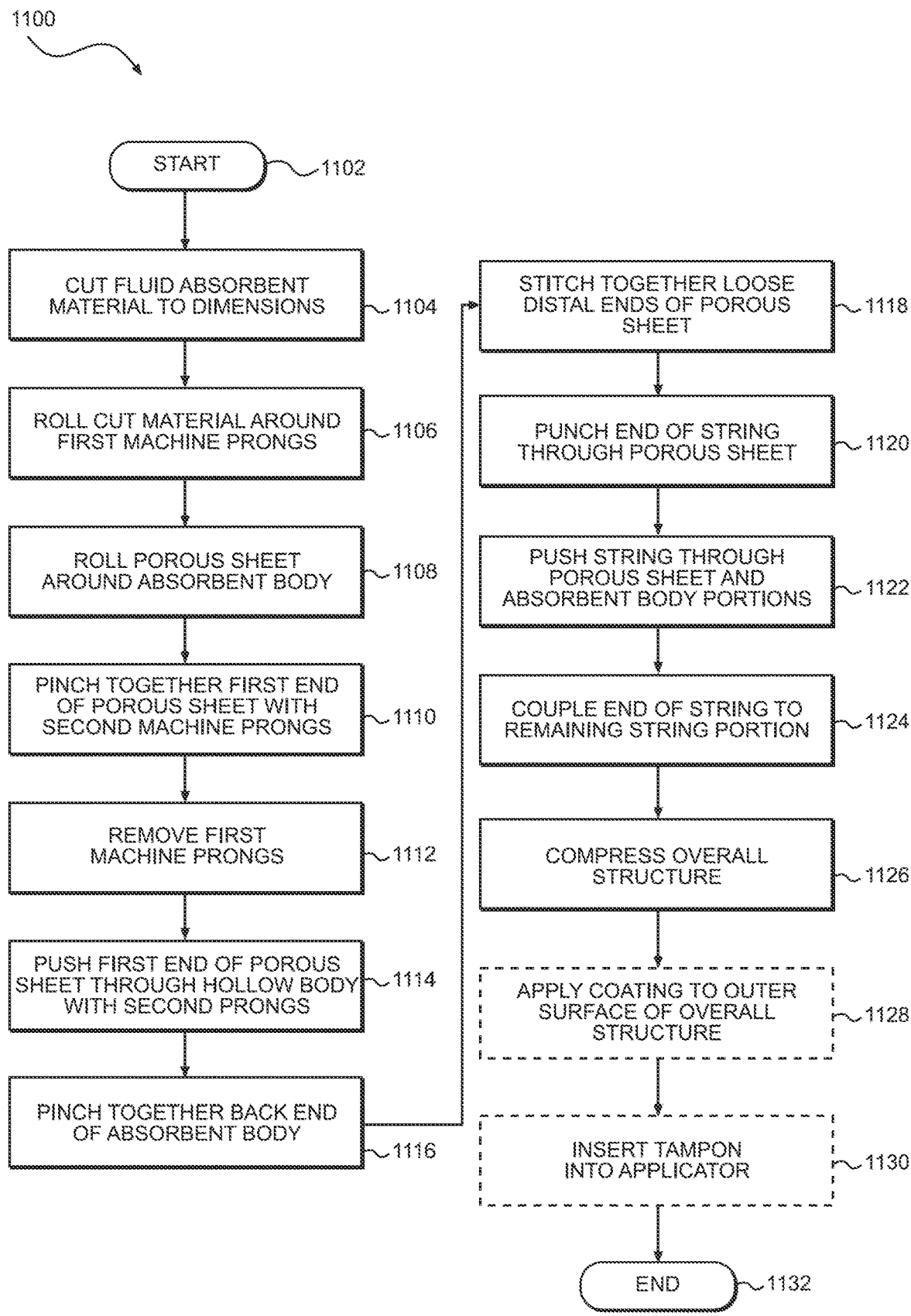
FIG. 11 illustrates a flowchart of an example detailed method of manufacturing a tubular shaped tampon according to one embodiment of the present disclosure.

Turning next to FIG. 11, a flowchart of an example method 1100 of manufacturing a tubular shaped tampon is provided. After a start step 1102, a fluid absorbent material can be cut to specific dimensions at process step 1104. This can correspond that which is shown in FIG. 3A above and the accompanying description.

At the next process step 1106, the cut material can be rolled around a first set of machine prongs. This can correspond that which is shown in FIG. 3B above and the accompanying description. At subsequent process step 1108, a porous sheet can be rolled around the absorbent body. This can correspond that which is shown in FIG. 3C above and the accompanying description.

At the next process step 1110, a first end of the porous sheet can be pinched together with a second set of machine prongs. This can correspond that which is shown in FIG. 4B above and the accompanying description.

At subsequent process step 1112, the first set of machine prongs can be removed, and at process step 1114 the pinched first end of the porous sheet can be pushed through the hollow body with the second set of machine prongs. Steps 1112 and 1114 can be performed simultaneously and can correspond that which is shown in FIGS. 4C-4E above and the accompanying description to arrive at a "blank" formation in the tampon manufacturing process.

At the next process step 1116, the back end of the absorbent body can be pinched together to form an overall cupped shape in the original tube shaped blank, and at the following process step 1118, the loose distal ends of the porous sheet can be stitched together. These steps can correspond that which is shown in FIGS. 6 and 7A-7D above and the accompanying description.

At the following process step 1120, a string end can be punched through the porous sheet, and at the next process step 1122, the string can be pushed through the porous sheet and absorbent body portions to exit at the opposite side of the overall tubular structure. At subsequent process step 1124, the end of the string can be coupled to a remaining string portion. These steps can correspond to that which is shown in FIGS. 8 and 9A-9B above and the accompanying description.

At the following process step 1126, the overall structure can be compressed. This can involve a primary compression phase (lateral) and a secondary compression stage (axial) to compress the overall structure both laterally and axially. This can also involve removing a finished tampon product from a compressor. This can correspond to that which is shown in FIGS. 10A-10C above and the accompanying description.

At the next optional process step 1128, a coating can be applied to the outer surface of the overall structure. This can be, for example, a cannabinoid oil applied by a coater. At the following optional process step 1130, the finished tampon can be inserted into an applicator. This can involve inserting the tampon product, with or without a coating, into an applicator, and may also include inserting a plunger into the applicator after the tampon product. This can correspond to FIGS. 10D-10F above and the accompanying description. The method then ends at end step 1132.

It will be appreciated that the foregoing methods 200 and 1100 may include additional steps not shown, and that not all steps are necessary in some embodiments. For example, additional steps may include formation of material sources, details regarding applicator components, and/or packaging a finished tampon product. Furthermore, the order of steps may be altered as desired, and one or more steps may be performed simultaneously. Other method steps, orders, and details may also be used to arrive at the disclosed tampon products.

While the foregoing example tampons and methods of making same have been disclosed for purposes of illustration, it will be appreciated that there may be other embodiments and variations in ways of making tubular shaped tampon products. It is specifically contemplated that all such variations for tubular or overall cup shaped tampon products and methods of making same be included herein. In one alternative embodiment, the protective sleeve can be double pushed through the hollow internal region of the absorbent material such that stitching may not be necessary to fully enclose the absorbent material and hold the protective sleeve in place. Various details of such an alternative arrangement follow.

Figure 12A:
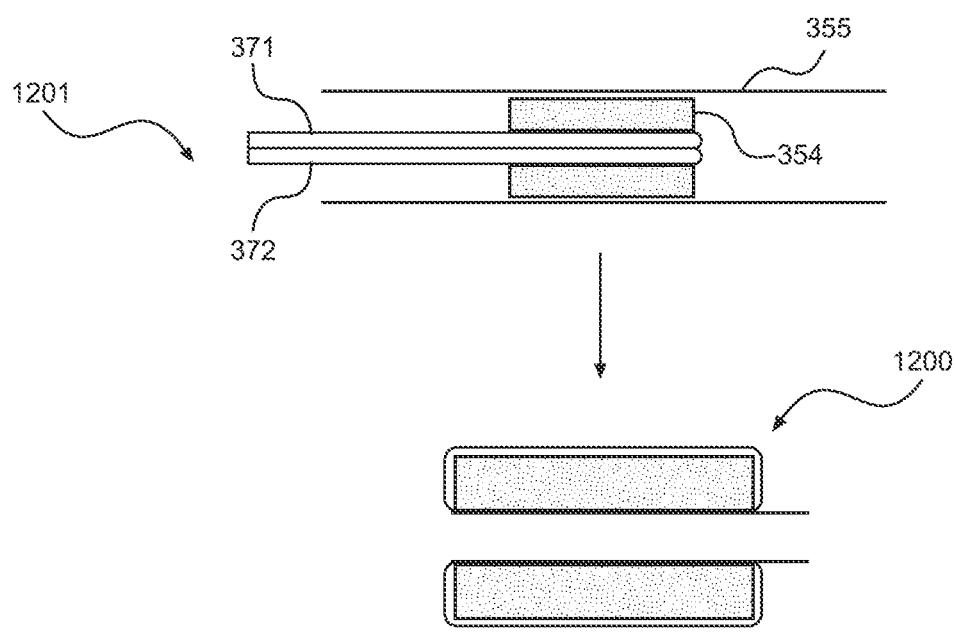
FIG. 12A illustrates in diagrammatic view an alternative process step of enclosing the absorbent body within the porous sheet according to one embodiment of the present disclosure.
Figure 12B:
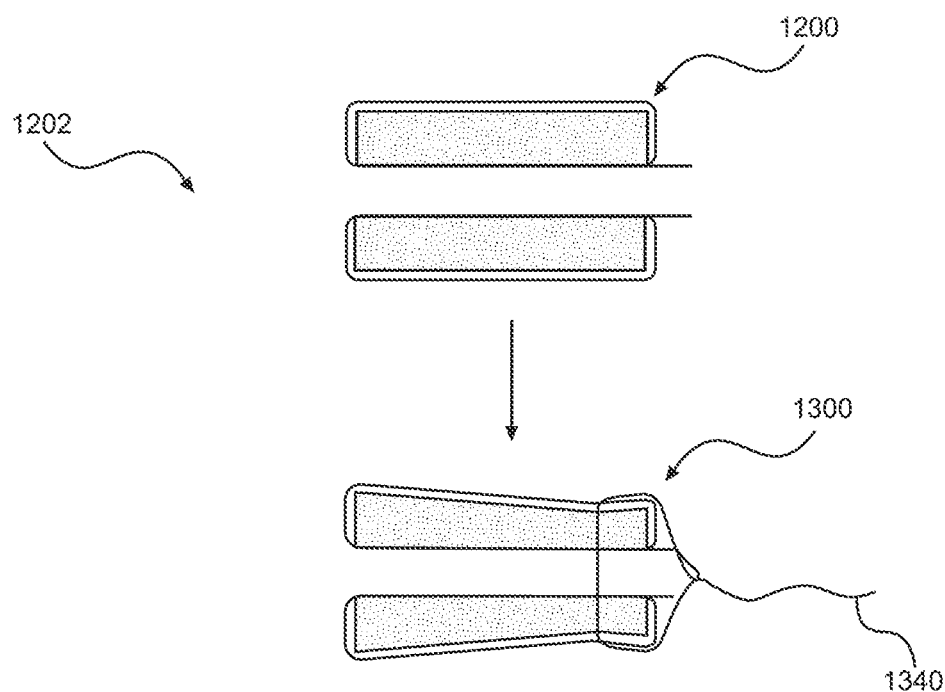
FIG. 12B illustrates in diagrammatic view an alternative process step of coupling a string to the absorbent body and porous sheet according to one embodiment of the present disclosure.

Transitioning to FIGS. 12A through 14D, an alternative way of enclosing the absorbent material in a protective sleeve will now be provided. FIG. 12A illustrates in diagrammatic view 1201 an alternative process step of enclosing the absorbent body within the porous sheet, which results in alternative partially formed tubular shaped tampon 1200. Details of how this can be accomplished are set forth below in FIGS. 13A-13J and the accompanying description. FIG. 12B illustrates in diagrammatic view an alternative process step of coupling a string to the absorbent body and porous sheet, which results in alternative partially formed string coupled tubular shaped tampon 1300.

Figure 13A:
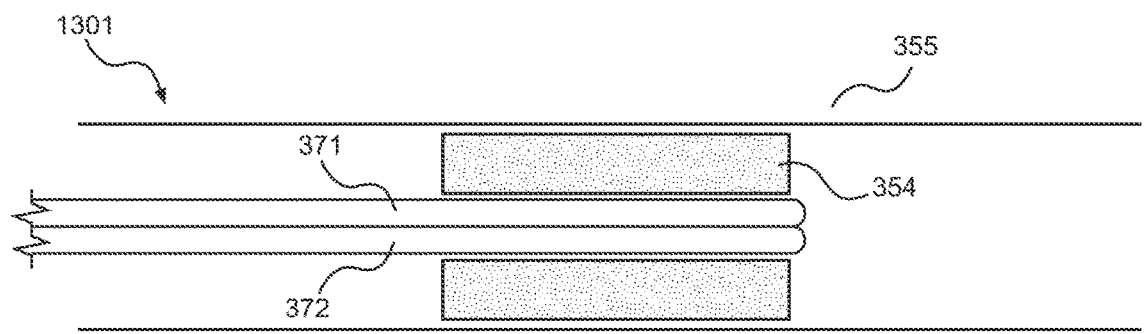
FIG. 13A illustrates in diagrammatic view an alternative subprocess step of beginning to enclose an absorbent body wrapped around a first set of machine prongs within a porous sheet according to one embodiment of the present disclosure.

Continuing with FIGS. 13A-13J, a detailed breakdown of an alternative way of enclosing the absorbent body within the porous sheet is shown in a series of progressing diagrammatic views. FIG. 13A illustrates in diagrammatic view 1301 a subprocess step of beginning to enclose an absorbent body wrapped around a first set of machine prongs within a porous sheet. FIG. 13A can correlate to the first portion of FIG. 3D above, with a porous sheet material 355 rolled around an absorbent material 354, which is in turn rolled around machine prongs 371, 372. The length of porous sheet material 355 can be substantially greater than the length of absorbent material 354, with the ends of the porous sheet material 355 extending significantly beyond both distal ends of the absorbent material 354.

Figure 13B:
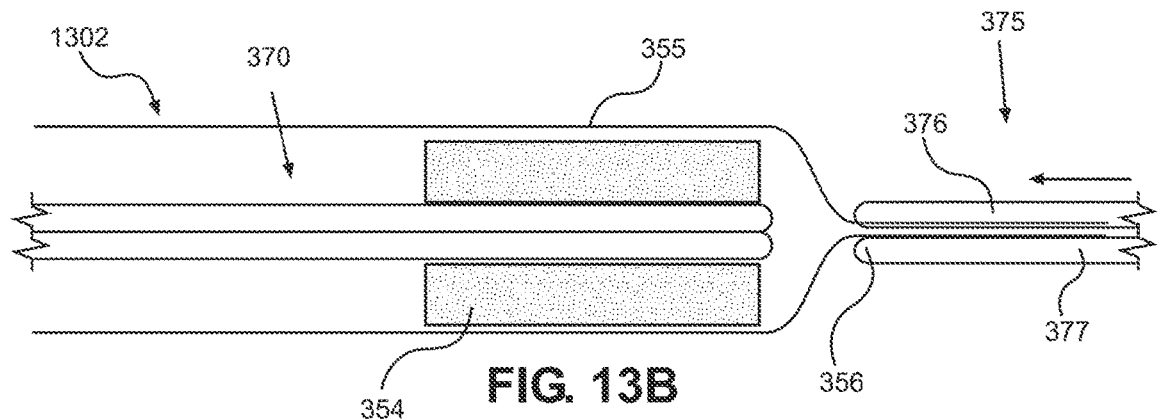
FIG. 13B illustrates in diagrammatic view an alternative subprocess step of pinching closed a first distal end of the porous sheet with a second set of machine prongs according to one embodiment of the present disclosure.

FIG. 13B illustrates in diagrammatic view 1302 a subprocess step of pinching closed a first distal end of the porous sheet with a second set of machine prongs. A second set of machine prongs 375, which can include prongs 376, 377, can be used to pinch together one end of the porous sheet material 355 that extends past a back distal end of the absorbent material to form pinched porous sheet end 356. Second set of machine prongs 375 can be identical or substantially similar to first set of machine prongs 370, such as by being formed from a medical grade material.

Figure 13C:
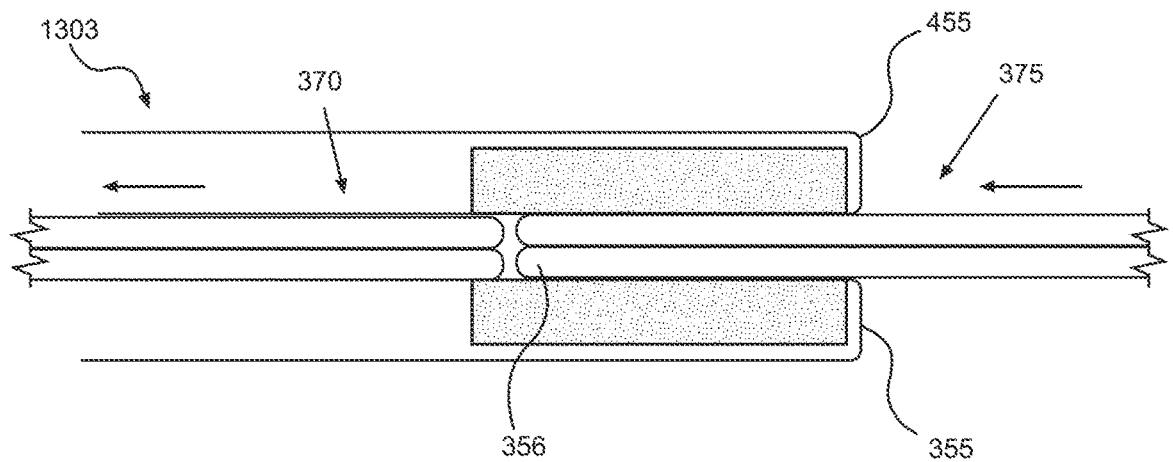
FIG. 13C illustrates in diagrammatic view alternative subprocess steps of removing the first set of machine prongs and pushing the pinched closed distal end of the porous sheet into the hollow region of the absorbent body with the second set of machine prongs according to one embodiment of the present disclosure.

FIG. 13C illustrates in diagrammatic view 1303 subprocess steps of removing the first set of machine prongs and pushing the pinched closed distal end of the porous sheet into the hollow region of the absorbent body with the second set of machine prongs. First set of machine prongs 370 can be removed from the hollow interior region of absorbent material 354, and second set of machine prongs 375 can then be inserted into the hollow region while still holding together pinched porous sheet end 356. This can result in porous sheet material 355 wrapping around from the top and bottom of the absorbent material 354 to cover the back distal end of the absorbent material and also the inner surfaces of the absorbent material along the hollow interior region.

Figure 13D:
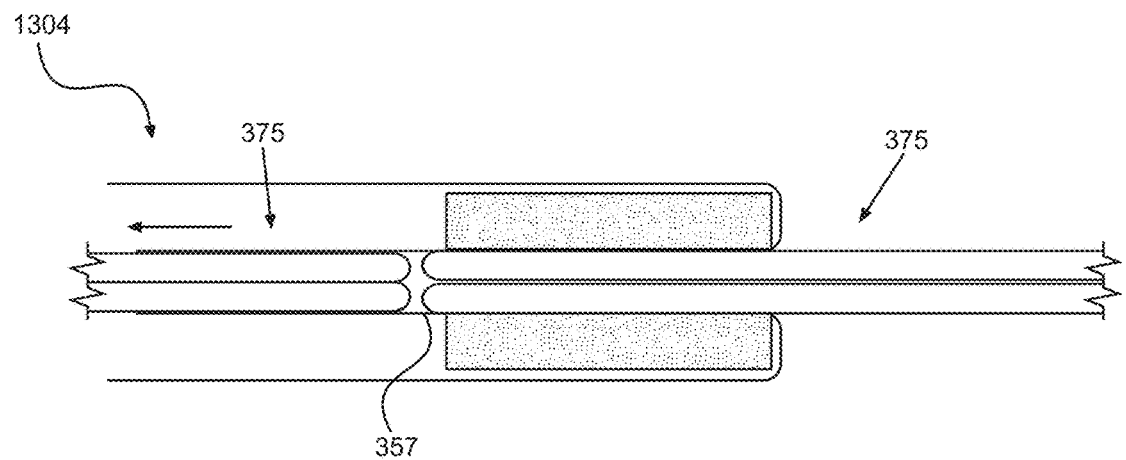
FIG. 13D illustrates in diagrammatic view an alternative subprocess step of pushing the pinched closed first distal end of the porous sheet fully through the hollow region and past the opposite distal end of the absorbent body according to one embodiment of the present disclosure.

FIG. 13D illustrates in diagrammatic view 1304 a subprocess step of pushing the pinched closed first distal end of the porous sheet fully through the hollow region and past the opposite distal end of the absorbent body. As second set of machine prongs 375 extends fully through the internal hollow region of the bulk absorbent material, the porous sheet can fully line the interior surfaces of the internal hollow region. Upon full extension, the distal end of the porous sheet can be released from the second set of machine prongs 375 to become unpinched together porous sheet end 357, which can extend past the front distal end of the bulk absorbent material. The second set of machine prongs 375 can open slightly to facilitate this release, or the porous sheet can simply slide out from the grasp of the machine prongs due to the porous sheet being fully extended.

Figure 13E:
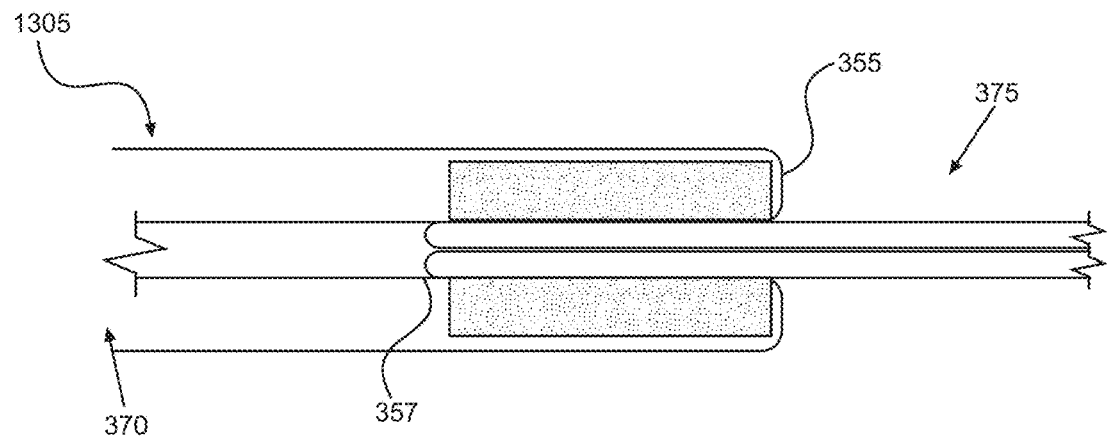
FIG. 13E illustrates in diagrammatic view an alternative subprocess step of fully removing the first set of machine prongs according to one embodiment of the present disclosure.
Figure 13F:
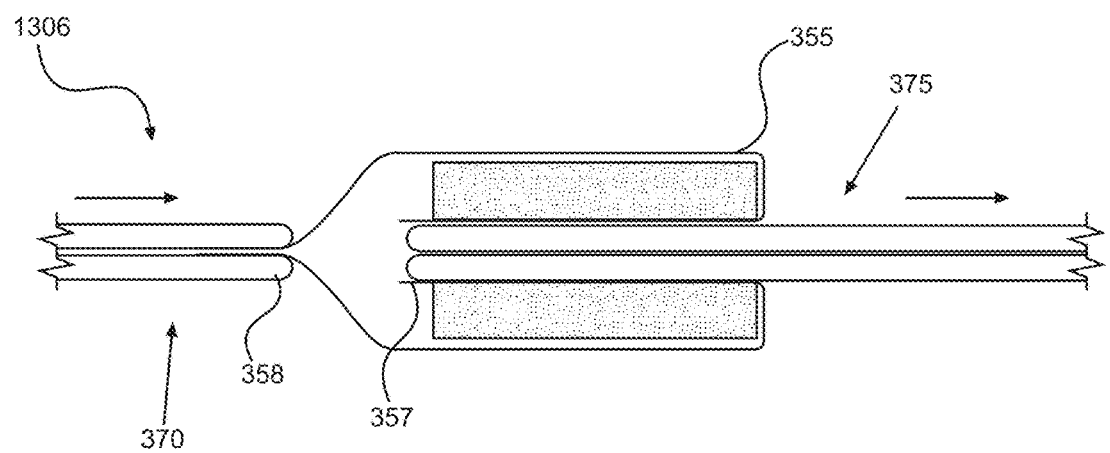
FIG. 13F illustrates in diagrammatic view an alternative subprocess step of pinching closed a second distal end of the porous sheet with the first set of machine prongs according to one embodiment of the present disclosure.

FIG. 13E illustrates in diagrammatic view 1305 a subprocess step of fully removing the first set of machine prongs. First set of machine prongs 370 can be fully removed from both the bulk absorbent material and the extended front distal end of porous sheet 355 while the second set of machine prongs 375 remains within the internal hollow region of the bulk absorbent material. FIG. 13F illustrates in diagrammatic view 1306 a process step of pinching closed a second distal end of the porous sheet with the first set of machine prongs. Once fully removed, first set of machine prongs 370 can then be opened, moved forward, and then closed to pinch together the front distal end of the porous sheet to form a second pinched together porous sheet end 358.

Figure 13G:
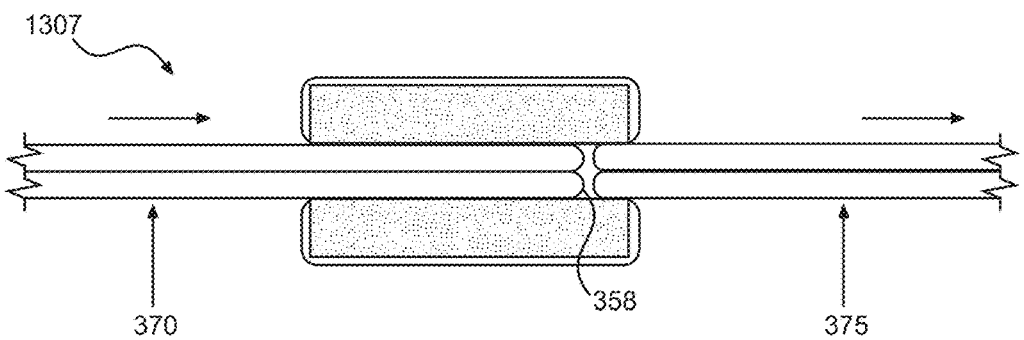
FIG. 13G illustrates in diagrammatic view alternative subprocess steps of removing the second set of machine prongs and pushing the second pinched closed distal end of the porous sheet into the hollow region of the absorbent body with the first set of machine prongs according to one embodiment of the present disclosure.

FIG. 13G illustrates in diagrammatic view 1307 subprocess steps of removing the second set of machine prongs and pushing the second pinched closed distal end of the porous sheet into the hollow region of the absorbent body with the first set of machine prongs. Similar to that which is shown in FIG. 13C above, second set of machine prongs 375 can be removed from the internal hollow region while first set of machine prongs 370 is inserted into the hollow region while holding together second pinched together porous sheet end 358. Due to the nature of the materials involved, the porous sheet initially lining the bulk absorbent material can tend to remain in place while the first set of machine prongs 370 pushes through another layer of the porous sheet to reline the internal hollow region. This can occur due to naturally higher friction between the fibrous absorbent material and fibrous porous sheet, and the naturally lower friction between the porous sheet and the smooth metal machine prongs. The unpinched together porous sheet end 357 can be neatly tucked under the second layer of porous sheet being pushed back through the internal hollow region by the first set of machine prongs 370.

Figure 13H:
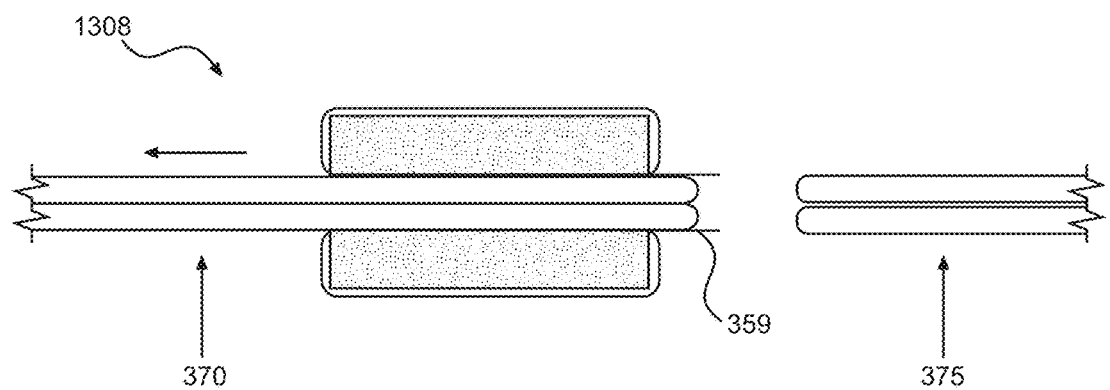
FIG. 13H illustrates in diagrammatic view an alternative subprocess step of pushing the pinched closed second distal end of the porous sheet fully through the hollow region and past the opposite distal end of the absorbent body according to one embodiment of the present disclosure.

FIG. 13H illustrates in diagrammatic view 1308 a subprocess step of pushing the pinched closed second distal end of the porous sheet fully through the hollow region and past the opposite distal end of the absorbent body. Similar to that which is shown in FIG. 13D above, the second set of machine prongs 375 can be fully removed from the hollow internal region while the first set of machine prongs pushes the second layer of porous sheet material through the internal hollow region until a second unpinched together porous sheet end 359 extends past the back distal end of the bulk absorbent material.

Figure 13I:
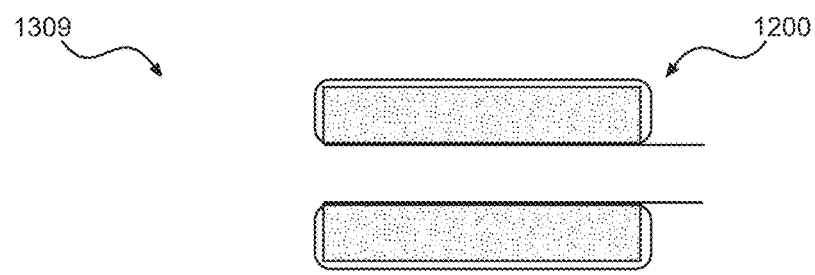
FIG. 13I illustrates in diagrammatic view an alternative subprocess step of removing both sets of machine prongs to leave a fully enclosed absorbent body according to one embodiment of the present disclosure.

FIG. 13I illustrates in diagrammatic view 1309 a subprocess step of removing both sets of machine prongs to leave a fully enclosed absorbent body. Both sets of machine prongs 370, 375 can then be fully removed from the bulk absorbent material and porous sheet to result in partially formed tubular shaped tampon 1200. As will be readily appreciated from the foregoing description, partially formed tubular shaped tampon 1200 can include bulk absorbent material formed into a tubular shape, with a porous sheet fully encapsulating the bulk absorbent material along all surfaces.

Figure 13J:
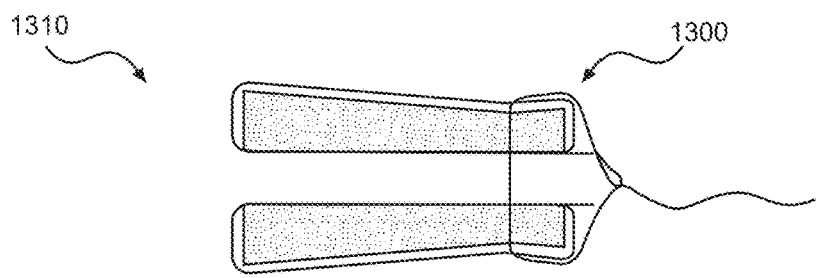
FIG. 13J illustrates in diagrammatic view an alternative subprocess step of attaching a string through the absorbent body and porous sheet combination according to one embodiment of the present disclosure.
Figure 14A:
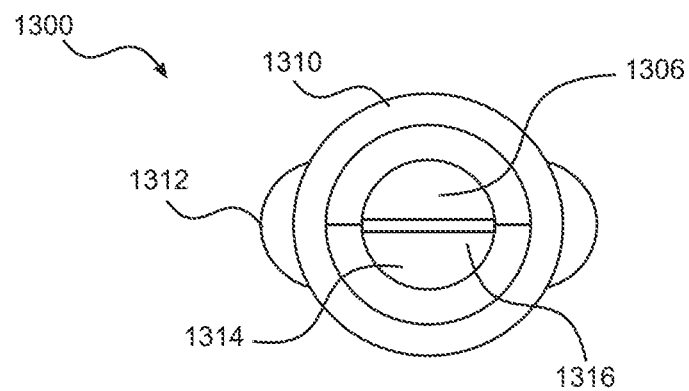
FIG. 14A illustrates in front elevation view an example alternative partially formed and string coupled tampon according to one embodiment of the present disclosure.
Figure 14B:
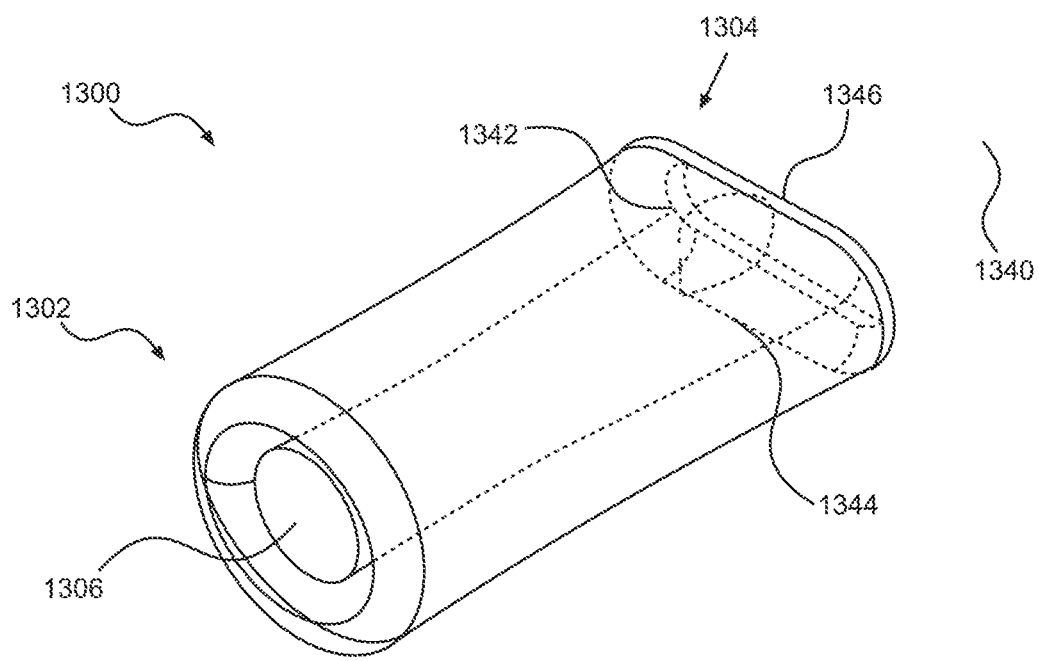
FIG. 14B illustrates in side perspective view the example alternative partially formed and string coupled tampon of FIG. 14A according to one embodiment of the present disclosure.
Figure 14C:
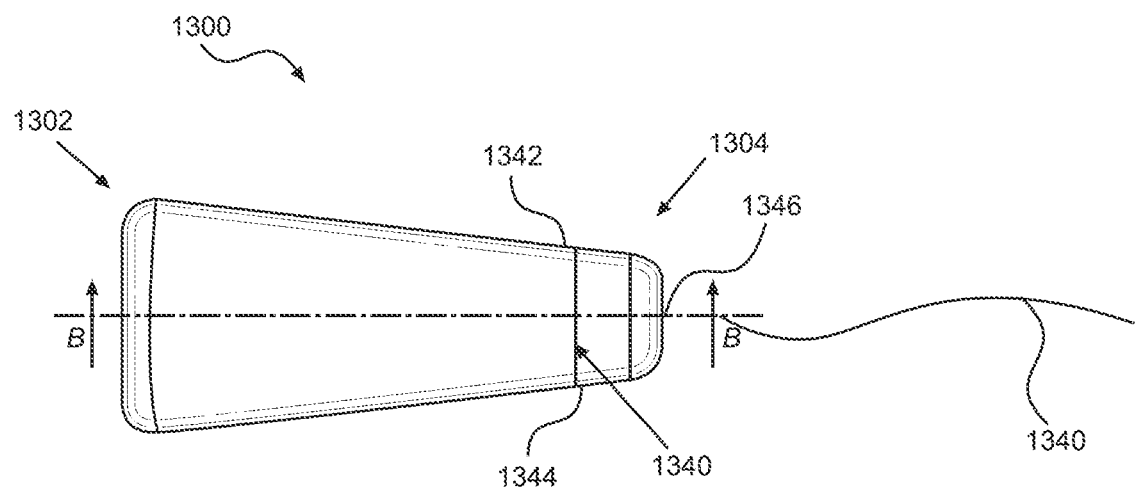
FIG. 14C illustrates in side elevation view the example alternative partially formed and string coupled tampon of FIG. 14A according to one embodiment of the present disclosure.
Figure 14D:
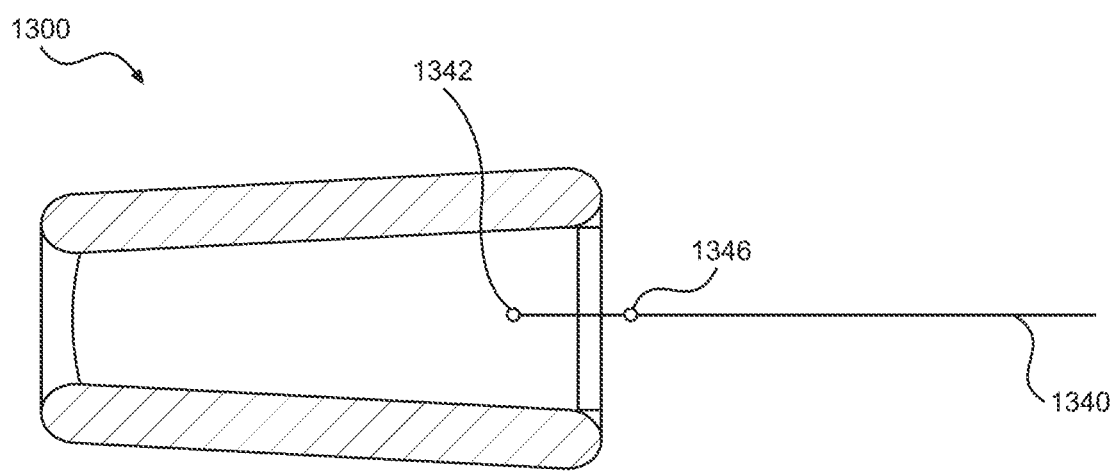
FIG. 14D illustrates in top cross-section view the example partially formed and string coupled tampon of FIG. 14A according to one embodiment of the present disclosure.

FIG. 13J illustrates in diagrammatic view 1310 a process step of attaching a string through the absorbent body and porous sheet combination. To hold the porous sheet in place against the bulk absorbent material at its back distal end, a string can be attached to arrive at alternative partially formed string coupled tubular shaped tampon 1300. This string can also function as a removal device after actual use of the finished tampon product. As noted above, the back distal end of partially formed tubular shaped tampon 1200 can be compressed as part of the string coupling process. Not only does this help to form a more secure attachment of the string to the partially formed tampon product, but it also shapes the back distal end of the tampon product to limit fluid flow through the internal hollow region. As such, menstrual fluids can flow into the internal hollow region via the front distal end of the finished tampon product during use, but are prevented from freely flowing out the back distal end of the finished tampon product due to the flattening of the back distal end and holding it shut with the string coupling.

FIGS. 14A-14D illustrate the alternative partially formed and string coupled tampon in front elevation, side perspective, side elevation, and top cross-section views respectively. Alternative partially formed and string coupled tubular shaped tampon 1300 can represent an alternative version of the foregoing finished tampon 100 at a particular stage of the manufacturing process. String 1340 can be coupled in a manner identical or substantially similar to the string coupling processes disclosed above.

As can be seen in FIGS. 14A-14D, back distal end 1304 of partially formed string coupled tubular shaped tampon 1300 can be squeezed together or flattened as part of the string coupling process. This can result in limiting the amount of fluids that can pass through the back distal end 1304 toward the string 1340 during use of the finished tampon product. As shown in the front elevation view from front distal end 1302 in FIG. 14A, overall tubular structure 1310 can be flattened from a fully round or tubular shape 1310 at the front distal end to a flattened shape with extending side bulges 1312 and flow blocking regions 1314 at the back distal end. Inner hollow region 1306 is thus flattened from a round shape at the front distal end to a narrow slit 1316 at the back distal end of partially formed and string coupled tubular shaped tampon 1300. String 1340 can also function to maintain this flattened shape when tightly applied.

Although the foregoing disclosure has been described in detail by way of illustration and example for purposes of clarity and understanding, it will be recognized that the above described disclosure may be embodied in numerous other specific variations and embodiments without departing from the spirit or essential characteristics of the disclosure. Certain changes and modifications may be practiced, and it is understood that the disclosure is not to be limited by the foregoing details, but rather is to be defined by the scope of the appended claims.

What is claimed is:

1. A method of creating a tampon, the method comprising:
   forming an absorbent body defining a cylindrical shape having an exterior surface, a hollow interior, an interior surface, and first and second opposing distal ends, the absorbent body having a fluid absorbent material;
   enclosing the absorbent body within a protective sleeve at the exterior surface, interior surface, and both distal ends, the protective sleeve being porous to allow fluid to enter the absorbent body but prevent absorbent body material from passing through the protective sleeve, wherein the absorbent body and protective sleeve combine to define an overall tubular structure having an inner hollow region and a first diameter, wherein enclosing the absorbent body within a protective sleeve includes:
      rolling a porous sheet around the absorbent body, wherein the porous sheet extends beyond both distal ends of the absorbent body at a length that exceeds the length of the absorbent body;
      pinching together a first distal end of the porous sheet that extends beyond the first distal end of the absorbent body; and
      pushing the pinched together first distal end of the porous sheet through the hollow interior and past the second distal end of the absorbent body, wherein the first distal end of the porous sheet and a second distal end of the porous sheet both extend past the second distal end of the absorbent body; and
   coupling a string to the protective sleeve, wherein the string facilitates removal of the tampon after use.

2. The method of claim 1, further comprising the step of:
   compressing the overall tubular structure to a second diameter that is less than the first diameter.

3. The method of claim 1, further comprising the step of:
   applying a coating to an outer surface of the overall tubular structure.

4. The method of claim 1, wherein forming the absorbent body includes:
   cutting a fluid absorbent material to a specific length and width;
   rolling the cut fluid absorbent material around a first set of elongated machine prongs; and
   removing the first set of elongated machine prongs.

5. The method of claim 4, wherein the fluid absorbent material is cotton.

6. The method of claim 1, wherein enclosing the absorbent body within a protective sleeve further includes:
   stitching together the first distal end and the second distal end of the porous sheet.

7. The method of claim 6, wherein enclosing the absorbent body within a protective sleeve further includes:
   pinching closed the second distal end of the absorbent body before stitching together the first distal end and the second distal end of the porous sheet.

8. The method of claim 1, wherein enclosing the absorbent body within a protective sleeve further includes:
   pinching together a second distal end of the porous sheet that extends beyond the second distal end of the absorbent body; and
   pushing the pinched together second distal end of the porous sheet through the hollow interior and past the first distal end of the absorbent body, wherein pushing the second distal end of the porous sheet tucks the first distal end of the porous sheet between the porous sheet and the absorbent body.

9. The method of claim 1, wherein coupling the string to the protective sleeve includes:
   punching an end of the string through a top outer surface of the protective sleeve;
   pushing the string through the protective sleeve, a top portion of the absorbent body, an inner surface of the protective sleeve, the hollow region, another inner surface of the protective sleeve, a bottom portion of the absorbent body, and out from a bottom outer surface of the protective sleeve; and
   coupling the end of the string to a remaining portion of the string that has not passed through the protective sleeve.

10. The method of claim 9, wherein coupling the end of the string includes passing the end of the string through a loop in the remaining portion of the string.

11. A method of manufacturing a tubular shaped tampon, the method comprising:
    cutting a fluid absorbent material to a specific length and width;
    rolling the cut fluid absorbent material around a first set of elongated machine prongs or an elongated rod, wherein the rolling forms an absorbent body defining a cylindrical shape having an exterior surface, a hollow interior, an interior surface, and first and second opposing distal ends;
    rolling a porous sheet around the absorbent body, wherein the porous sheet extends beyond both distal ends of the absorbent body;
    pinching together using a second set of elongated machine prongs a first distal end of the porous sheet that extends beyond the first distal end of the absorbent body;
    pushing using the second set of elongated machine prongs the pinched together first distal end of the porous sheet through the hollow interior and past the second distal end of the absorbent body, wherein the first distal end of the porous sheet and a second distal end of the porous sheet both extend past the second distal end of the absorbent body;
    removing the first set of elongated machine prongs or elongated rod while pushing using the second set of elongated machine prongs;
    pinching closed the second distal end of the absorbent body;
    stitching together the first distal end and the second distal end of the porous sheet such that the porous sheet then forms a protective sleeve enclosing the absorbent body, wherein the absorbent body and protective sleeve combine to define an overall tubular structure having an inner hollow region and a first diameter;

punching an end of a string through a top outer surface of the protective sleeve;

pushing the string through the protective sleeve, a top portion of the absorbent body, an inner surface of the protective sleeve, the hollow region, another inner surface of the protective sleeve, a bottom portion of the absorbent body, and out from a bottom outer surface of the protective sleeve; and coupling the end of the string to a remaining portion of the string that has not passed through the protective sleeve.

12. The method of claim 11, further comprising the steps of:

compressing the overall tubular structure to a second diameter that is less than the first diameter; and applying a coating to an outer surface of the overall tubular structure.

\* \* \* \* \*